United States Patent [19]
Mazodier et al.

[11] Patent Number: 6,153,404
[45] Date of Patent: *Nov. 28, 2000

[54] REGULATORY NUCLEOTIDE SEQUENCE OF THE INITIATION OF TRANSCRIPTION

[75] Inventors: Philippe Mazodier, Clamart; Gérard Guglielmi, Levallois-Perret, both of France

[73] Assignee: Institut Pasteur, Paris, France

[*] Notice: This patent is subject to a terminal disclaimer.

[21] Appl. No.: 09/031,606

[22] Filed: Feb. 27, 1998

Related U.S. Application Data

[62] Division of application No. 08/461,775, Jun. 5, 1995, Pat. No. 5,858,773, which is a continuation of application No. 08/050,313, filed as application No. PCT/FR91/00701, Sep. 3, 1991, abandoned.

[30] Foreign Application Priority Data

Sep. 10, 1990 [FR] France ................................ 90 11186

[51] Int. Cl.⁷ ........................... C12N 15/11; C12N 15/63; C12N 1/20; C07H 21/04
[52] U.S. Cl. ..................... 435/69.1; 435/455; 435/255; 435/320.1; 435/253.5; 536/23.1; 536/24.1
[58] Field of Search ................. 536/23.1, 24.1; 435/455, 377, 255, 325, 320.1, 69.1, 253.5; 530/350

[56] References Cited

U.S. PATENT DOCUMENTS 4,797,349  1/1989  Finkelstein ................ 435/68

FOREIGN PATENT DOCUMENTS

| 0 179 449 | 4/1986 | European Pat. Off. . |
| 0 352 707 | 1/1990 | European Pat. Off. . |
| 0352707 A2 | 1/1990 | European Pat. Off. . |

OTHER PUBLICATIONS

*The Journal of Antibiotics*, "Cloning of DNA Fragments Containing *Streptomyces* Promoter Activity", Taichi Manome et al, Oct. 1987, vol. XL, No. 10, pp. 1440–1447.

*Gene*, "Nucleotide Sequence of the Putative Regulatory Gene and Major Promoter Region of the *Streptomyces griseus* Glycerol Operon", Alexander Bolotin, et al, 1990, vol. 87, pp. 151–152.

*Gene*, "Two Promoters from the *Streptomyces* Plasmid plJ101 and Their Expression in *Escherichia coli*", Mark J. Buttner, et al, 1987, vol. 51, pp. 179–186.

*Molecular Biology*, "Post–Transcriptional Regulation of the groEl1 gene of *Streptomyces albus*", P. Servant, et al., (1994), 12(3), pp. 423–432; and *Journal of Bacteriology*, "Characterization of *Streptomyces albus* 18–Kilodalton Heat Shock–Responsive Protein", P. Servan et al., Jun. 1995, vol. 177, No. 11, pp. 2998–3003.

M. Hecker, et al., "Heat–shock and General Stress Response in *Bacilus subtilis*," *Molecular Microbiology*, 19(3):417–428 (1966).

A. Duchêne, et al., "Transcriptional Analysis of groEL Genes of *Streptomyces coelicolor* A3(2)," 245:61–68 (1994).

Baird et al "Cloning and Sequence Analysis of the 10kDa Antigen Gene of *Mycobacterium tuberculosis*" J. of General Microbiology vol. 135: 931–939, 1989.

*Primary Examiner*—Remy Yucel
*Assistant Examiner*—Sean McGarry
*Attorney, Agent, or Firm*—Burns, Doane, Swecker & Mathis, LLP

[57] ABSTRACT

The invention relates to a recombinant nucleotide sequence, characterized in that it comprises:

a regulatory sequence of the initiation of tanscription, this regulatory sequence containing a promoter in association with the motif GCACTC 9N GAGTGC, in which "N" signifies any one of the 4 bases thymine, guanine, adenine and cytosine;

a sequence coding for a polypeptide, called "heterologous polypeptide", which is different from that naturally associated with the said promoter;

the said coding sequence being positioned downstream from the said regulatory sequence of the initiation of transcription at a site which, under suitable conditions, would allow the expression of the polypeptide under the control of the said promoter.

19 Claims, 16 Drawing Sheets

P1:
CATTGGCACTCCGCTTGACCGAGTGCTAATCGCGGTCATAGTCTCAGCTCTG
5'                                                                                                                3'

-30                              -10         +1
GCATTGGCACTCCGCTTGACCGAGTGCTAATCGCGGTCATAGTCTCAGCTCTG
5'                                                                                                                3'

P2:
GGAGGCCCCTAGCGCCTGCACTCTCCTACCCGAGTGCTATTATTGGCGTTA
5'                                                                                                                3'

-30                              -10         +1
GGAGGCCCCTAGCGCCTGCACTCTCCTACCCGAGTGCTAATTATTGGCGTTA
5'                                                                                                                3'

CONSENSUS MOTIF    :GCACTC    7N    CCGAGTGCTAAT

PALINDROMIC CONSENSUS MOTIF    :GCACTC 9N GAGTGC

FIG. 2

```
1/1
GTG ACG ACC GCC AGC TCC AAG GTT GCC ATC AAG CCG CTC GAC GAG CGC ATC GTG GTC CAG
val thr thr ala ser ser lys val ala ile lys pro leu glu asp arg ile val val gln
61/21                                               31/11
CCG CTC GAC GCC GAG CAG ACC ACG GCT TCG GGC CTG GTC GAC ACC GCG AAG GAG
pro leu asp ala glu gln thr thr ala ser gly leu val ile pro asp thr ala lys glu
121/41                                              91/31
AAG CCC CAG GAG GGC GTC CTC GCG GTC CTC GGC CCG GGC TTC GAG AAC GGC GAG CGC
lys pro gln glu gly val leu ala val leu gly pro gly arg phe glu asn gly glu arg
181/61                                              151/51
CTG CCG CTC GAC GTC AAG ACC GGC GAC CTC GTG CTG TAC AGC AAG TAC GGC GGC ACC GAG
leu pro leu asp val lys thr gly asp leu val leu tyr ser lys tyr gly gly thr glu
241/81                                              211/71
GTC AAG TAC AAC GGC GAG GAG TAC CTC GTC GCC CGC CTC TCG GCC CGC GTT CTC GCC ATC ATC
val lys tyr asn gly glu glu tyr leu val leu ser ala arg asp val leu ala ile ile
301/101                                             271/91
GAG AAG TAG
glu lys AMB
```

FIG.5

1/1
ATG GCG AAG ATT CTG AAG TTC GAC GAG GAC GCC GCC CGT CGC GCC CTT GAG CGC GGC GTG AAC
Met ala lys ile leu lys phe asp glu asp ala arg arg ala leu glu arg gly val asn
61/21                                                   31/11
CAG CTG GCC GAC ACC GTC AAG GTG ACC ATC GGC CCC AAG GGC CGC AAC GTC GTC ATC GAC
gln leu ala asp thr val lys val thr ile gly pro lys gly arg asn val val ile asp
122/41                                      91/31
AAG AAG TTC GGC GCC CCG ACC ATC ACC AAC GAC GGC GTC ACC ATC GCC CGT GAG GTC GAG
lys lys phe gly ala pro thr ile thr asn asp gly val thr ile ala arg glu val glu
181/61                                      151/51
TGC GAC GAC CCG TAC GAG AAC CTC GGC GCC CAG CTC GTC AAG GAG GTG GCG ACC AAG ACC
cys asp asp pro tyr glu asn leu gly ala gln leu val lys glu val ala thr lys thr
241/81                                      211/71
AAC GAC ATC GCG GGT GAC GGC ACC ACC GCG ACC GTG CTG GCC CAG GCG CTG GTC CGC
asn asp ile ala gly asp gly thr thr ala thr val leu ala gln ala leu val arg
301/101                                     271/91
GAG GGC CTG CGC AAC GTC GCC GCC GGC GCC AAC CCG ATG GCC CTG AAG AAG GGC ATC GAC
glu gly leu arg asn val ala ala gly ala asn pro ala ala leu lys lys gly ile asp
361/121                                     331/111
GCC GCC GTC GCC GCC GTC TCC GCC GTC CTG GAG CTC GAC ACC CGC CCG ATC GAC GAC AAG
ala ala val ala ala val ser ala val leu glu leu asp thr ala arg pro ile asp asp lys
421/141                                     391/131
TCC GAC ATC GCC GCC GCG CTC TCC GCG CAG GAC AAG CAG GTC GCG CAG AAG CAG GTC GGC GAG CTC ATC
ser asp ile ala val ala leu ser ala leu gln asp lys gln val ala gln lys gln val gly glu leu ile
                                            451/151
FIG. 6A

```
481/161
GCC GAG GCG ATG GAC AAG GTC GGC AAG GAC GGT GTC ATC ACC GTC GAG GAG TCC AAC ACC
ala glu ala met asp lys val gly lys asp gly val ile thr val glu glu ser asn thr
541/181                                                 511/171
TTC GGT GTC GAC CTG GAC TTC ACC GAG GGC ATG GCC TTC GAC AAG GGC TAC CTG TCC CCG
phe gly val asp leu asp phe thr glu gly met ala phe asp lys gly tyr leu ser pro
601/201
TAC ATG GTG ACC GAC CAG GAG CGT ATG GAG CGT CTC GAC GAC CCG TAC ATC CTG ATC
tyr met val thr asp gln glu arg met glu ala val leu asp asp pro tyr ile leu ile
661/221
CAC CAG GGC AAG ATC GGT TCG ATC CAG GAC CTG CTG CCG CTG CTG GAG AAG GTC ATC CAG
his gln gly lys ile gly ser ile gln asp leu leu pro leu leu glu lys val ile gln
721/241
GCG GGT GGC TCC AAG CCG CTG ATC ATC ATC GCC GAG GAC GTC GAG GGC GAG GCC CTG TCG
ala gly gly ser lys pro leu ile ile ile ala glu asp val glu gly glu ala leu ser
781/261
ACC CTG GTC AAC AAG ATC CGC GGC ACG TTC AAC GCC TTC AAC GCC GTC AAG GCG CCC GGC
thr leu val asn lys ile arg gly thr phe asn ala val ala val lys ala pro gly
841/281                                                 811/271
TTC GGT GAC CGC CGC AAG CGC ATG GCG ATG CTC GGC GAC ATG GCC ACC CTC ACC GGT GTC
phe gly asp arg arg lys arg met ala met leu gly asp met ala thr leu thr gly val
901/301                                                 871/291
ATC GCC GAG GAG GTC GGC CTC AAG CTC GAC CAG CTC GAC GTG CTG GAC GTG CTG GGC ACC GCC
Ile ala glu glu val gly leu lys leu asp gln ala gly leu asp val leu gly thr ala
                                                        931/311
```

FIG. 6B

961/321
CGC CGC GTC ACC GTC ACC AAG GAC GAC ACG ACC ATC GTG GAC GGC GGC AAC GCC GAG
arg arg val thr val thr lys asp asp thr thr ile val asp gly gly asn ala glu
1021/341

991/331
GAC GTC CAG GGC CGC GTC GCC CAG ATC AAG GCC GAG ATC GAG TCG ACC GAC TGG
asp val gln gly arg val ala gln ile lys ala glu ile glu ser thr asp trp
1081/361

GAG CGC GAG AAG CTC CAG GAG CGC CTC GCC GGC GTC TGC GTG ATC CGC
asp arg gln lys leu gln glu arg leu ala lys leu ala gly gly val cys val ile arg
1141/381

GTC GGC GCG GCC ACC GAG GTC GAG CTG AAG CGC AAG CAC CGT CTG GAG GAC GCC ATC
val gly ala ala thr glu val glu leu lys glu arg lys his arg leu glu asp ala ile
1201/401

TCC GCG ACC CGC GCG GCG GTC GAG GGC GTC TCC GGT GGC GGC GGC TCC GCG CTG GTC
ser ala thr arg ala ala val glu gly val ser gly gly gly ser ala leu val
1261/421

CAC GCC GTC AAG GTC CTG GAC GAC AAC CTC GGC CGC ACC GGC GAC GAG GCC ACC GGT GTC
his ala val lys val leu asp asp asn leu gly arg thr gly asp glu ala thr gly val

FIG. 6C

```
   1 CCGGCCGGGC TGAGGTTGGC TGGCTGGCCG GGTTCGGCCG GTGGGTCGAG GTGGCCTGGC   60
  61 CGGGCTCGCC AGGGTGAGTT GGCCGAGCCG AGGCGGCCCC GGGCCTCCCC GGCCGAGTT  120
 121 GGCGCGGCCA GGCCAGGGCT CAGCAGGGTG GGGGAGTGGG GCAGGCGGCC CGGTAGGGGA  180
 181 GTGCGGGAGG GCAGCGCGCG CCGCGCGCAT TGGCACTCCG CTTGACCGAG TGCTAATCGC  240
 241 GGTCATAGTC TCAGCTCTGG CACTCCCCGC AGGAGAGTGC CAACACAGCG ACGGGCAGGT  300
 301 CCGGCACCCG CGACGACGGA TCGACCTGGT CGCCACACTC AGATCAGTTA ACCCCGTGAT  360
 361 CTCCGAAGGG GGAGGTCGGA TCGTGACGAC CGCCAGCTCC AAGGTTGCCA TCAAGCCGCT  420
 421 CGAGGACCGC ATCGTGGTCC AGCCGCTCGA CGCCGAGCAG ACCACGGCTT CGGGCCTGGT  480
 481 CATCCCGGAC ACCGCGAAGG AGAAGCCCCA CGCCGAGCAG GAGGGGCGTC TCGGCCCGGG  540
 541 CCGCTTCGAG AACGGCGAGC GCCTGCCGCT CGACGTCAAG ACCGGCGACG TCGTGCTGTA  600
 601 CAGCAAGTAC GGCGGCACCG AGGTCAAGTA CAACGGCGAG GAGTACCTCG TCCTCTCGGC  660
 661 CCGCGACGTT CTCGCCATCA TCGAGAAGTA GCAGGCCCGA GCGGTCCGGG CGGAGCCCG  720
 721 GACGGCAGAC TCCACCTTTT TCCTGAAGCG CGCCCCTGGC CCCCGCGAGT GTTTGCCGGG  780
 781 TGGCGAGGGG CGCCTTTCAT TTCGAGAGCG CGGCGGCAGG CCGTCCGAG AGGATTCGAA  840
 841 AAGCTCCCAT GGCGAAGATT CTGAAGTTCG ACGAGGACGC CCGTCGCGCC CTTGAGCGCG  900
 901 GCGTGAACCA GCTGGCCGAC ACCGTCAAGG TGACCATCGG CCCCAAGGGC CGCAACGTCG  960
 961 TCATCGACAA GCCCCGACCA GCCCGCCCCA TCACCAACGA CGGCGTCACC ATCGCCCGTG 1020
1021 AGGTCGAGTG CGACGACCCG TACGAGAACC TCGGCGCCCA GCTCGTCAAG GAGGTGGCGA 1080
```

FIG. 7A

```
1081  CCAAGACCAA  CGACATCGCG  GGTGACGGCA  CCACCACCGC  GACCGTGCTG  GCCCAGGCGC  1140
1141  TGGTCCGCGA  GGGCCTGCGC  AACGTCGCCG  CCGGCGCCTC  CCCGGCCGCC  CTGAAGAAGG  1200
1201  GCATCGACGC  CGCCGTCGCC  GCCGTCTCCG  CCGAGCTGCT  CGACACCGCG  CGCCCGATCG  1260
1261  ACGACAAGTC  CGACATCGCC  GCCGTCGCCG  CGCTCTCCGC  GCAGGACAAG  CAGGTCGGCG  1320
1321  AGCTCATCGC  CGAGGGCGATG  GACAAGGTCG  GCAAGGACGG  TGTCATCACC  GTCGAGGAGT  1380
1381  CCAACACCTT  CGGTGTCGAC  CTGGACTTCA  CCGAGGGCAT  GGCCTTCGAC  AAGGCTACC  1440
1441  TGTCCCCGTA  CATGGTGACC  GACCAGGAGC  GTATGGAGGC  CGTCCTCGAC  GACCCGTACA  1500
1501  TCCTGATCCA  CCAGGCAAG   ATCGGTTCGA  TCCAGGACCT  GCTGCCGCTG  CTGGAGAAGG  1560
1561  TCATCCAGGC  GGGTGGCTCC  AAGCCGCTGC  TGATCATCGC  CGAGGACGTC  GAGGGCGAGG  1620
1621  CCCTGTCGAC  CCTGGTGGTC  AACAAGATCC  GCGGCACGTT  CAACGCCGTC  GCCGTCAAGG  1680
1681  CGCCCGGCTT  CGGTGACCGC  CGCAAGGCGA  TGCTGCAGGA  CATGGCCACC  CTCACCGGTG  1740
1741  CCACCGTCAT  CGCCGAGGAG  GTCGGCCTCA  AGCTCGACCA  GGCCGGTCTG  GACGTGCTGG  1800
1801  GCACCGCCCG  CCGCGTCACC  GTCACCAAGG  ACGACACGAC  CATCGTGGAC  GGCGGCGGCA  1860
1861  ACGCCGAGGA  CGTCCAGGGC  CGCGAGAAAG  CGCTGCCGCC  AGATCAAGGC  TCGACCGACT  1920
1921  CGGACTGGGA  CCGCGAGAGC  CTCCAGGAGC  GCCTTCGCCAA  GCCTGCCGGC  GGCGTCTGCG  1980
1981  TGATCCGCGT  CGGCGGCGCC  ACCGAGGTCG  AGCTGAAGGA  GCGCAAGCAC  CGTCTCTGGA  2040
2041  ACGCCATCTC  CGGCGACCCGC  AGGAGGGCAT  CGTCTCCGGT  GGTGGCTCCG  GTTGGCTCCG  2100
2101  CGCTGGTCCA  CGCCGTCAAG  CGCCGTCCAAG  ACAACCTCGG  CCGCACCGGC  GACGAGGCCA  2160
2161  CCGGTGT                                                                 2196
```

FIG. 7B

1/1
ATG GCG AAG ATT CTG AAG TTC GAC GAG GAC CGT CGC GCC CTT GAG CGC GGC GTG AAC
Met ala lys ile leu lys phe asp glu asp arg arg ala leu glu arg gly val asn
61/21                                       31/11
CAG CTG GCC GAC ACC GTC AAG GTG ACC ATC GCC AAG GGC CGC AAC GTC GTC ATC GAC
gln leu ala asp thr val lys val thr ile ala lys gly arg asn val val ile asp
121/41                                      91/31
AAG AAG TTC GGC GCC CCG ACC ATC ACC AAC GAC GGC GTC ACC ATC GCC CGT GAG GTC GAG
lys lys phe gly ala pro thr ile thr asn asp gly val thr ile ala arg glu val glu
181/61                                      151/51
TGC GAC GAC CCG TAC GAG AAC CTC GGC GCC CAG CTC GTC AAG GAG GTG GCG ACC AAG ACC
cys asp asp pro tyr glu asn leu gly ala gln leu val lys glu val ala thr lys thr
241/81                                      211/71
AAC GAC ATC GCG GGT GAC GGC ACC ACC GTG CTG GCG CAG CCG CTG GTC CGC
asn asp ile ala gly asp gly thr thr val leu ala gln ala leu val arg
301/101                                     271/91
GAG GGC CTG CGC AAC GTC GCC GCC GGC GCC AAG AAG GGC ATC GAC
glu gly leu arg asn val ala ala gly ala leu lys lys gly ile asp
361/121                                     331/111
GCC GCC GTC GCC GCC GTC TCC GCC GAG CTG CTC GAC ACC GCG CGC CCG ATC GAC GAC AAG
ala ala val ala ala val ser glu leu leu asp thr ala arg pro ile asp asp lys
                                            391/131

FIG.8A

```
421/141
TCC GAC ATC GCC GCC GTC GCC GCG CTC TCC GCG CAG GAC AAG CAG GTC GGC GAG CTC ATC
ser asp ile ala ala val ala ala leu ser ala gln asp lys gln val gly glu leu ile
                                                451/151
481/161
GCC GAG GCG ATG GAC AAG GTC GGC AAG GAC GGT GTC ATC ACC GTC GAG GAG TCC AAC ACC
ala glu ala met asp lys val gly lys asp gly val ile thr val glu glu ser asn thr
                                                511/171
541/181
TTC GGT GTC GAC CTG GAC TTC ACC GAG GGC ATG GCC TTC GAC AAG GGC TAC CTG TCC CCG
phe gly val asp leu asp phe thr glu gly met ala phe asp lys gly tyr leu ser pro
                                                571/191
601/201
TAC ATG GTG ACC GAC CAG GAG CGT ATG GAG GCC GTC CTC GAC CTG GAG AAG GTC ATC CAG
tyr met val thr asp gln glu arg met glu ala val leu asp leu glu lys val ile gln
                                                631/211
661/221
CAC CAG GGC AAG ATC GGT TCG ATC CAG GAC CTG CTG CCG CTG CTG GAG GAC GTC ATC CAG
his gln gly lys ile gly ser ile gln asp leu leu pro leu leu glu asp val ile gln
                                                691/231
721/241
GCG GGT GGC TCC AAG CCG AAG CTG ATC ATC ATC GCC GAG GAC GTC GAG GGC GAG GCC CTG
ala gly gly ser lys pro lys leu ile ile ile ala glu asp val glu gly glu ala leu
                                                751/251
781/261
ACC CTG GTG GTC AAC AAG ATC CGC GGC ACG TTC AAC GCC GTC GCC GTC AAG GCG CCC GGC
thr leu val val asn lys ile arg gly thr phe asn ala val ala val lys ala pro gly
                                                811/271
```

FIG. 8B

```
841/281
TTC GGT GAC CGC CGC AAG GCG ATG CTC GGC GAC ATG GCC ACC CTC ACC GGT GCC ACC GTC
phe gly asp arg arg lys ala met leu gly asp met ala thr leu thr gly ala thr val
901/301                                                         871/291
ATC GCC GAG GAG GTC GGC CTC AAG CTC GAC CAG GCC GGT CTG GAC GTG CTG GGC ACC GCC
ile ala glu glu val gly leu lys leu asp gln ala gly leu asp val leu gly thr ala
                                    931/311
CGC CGC GTC ACC GTC ACC AAG GAC GAC ACG ACC ATC GTG GAC GGC GGC GGC AAC GCC GAG
arg arg val thr val thr lys asp asp thr thr ile val asp gly gly gly asn ala glu
961/321
GAC GTC CAG GGC CGC GTC GCC CAG ATC GCC GAG ATC AAG GCC GAG TCG ACC GAC TCG GAC TGG
asp val gln gly arg val ala gln ile ala glu ile lys ala glu ser thr asp ser asp trp
1021/341                                            1051/351
GAC CGC GAG AAG CTC CAG GAG CGC CTC GCC AAG CTG GCC GGC GTC TGC GTG ATC CGC
asp arg glu lys leu gln glu arg leu ala lys leu ala gly gly val cys val ile arg
1081/361                                            1111/371
GTC GGC GCC GCC ACC GAG GCC GTC GAG CTG AAG GAG CGC AAG CAC CGT CTG GAG GAC GCC ATC
val gly ala ala thr glu ala val glu leu lys glu arg lys his arg leu glu asp ala ile
1141/391                                            1171/391
TCC GCG ACC CGC GCC GCG GTC GAG GAG GGC ATC GTC TCC GGT GGC GGC TCC GCG CTG GTC
ser ala thr arg ala ala val glu glu gly ile val ser gly gly gly ser ala leu val
1201/401                                            1231/411
```

FIG. 8C

1261/421
CAC GCC GTC AAG GTC CTG GAC GAC AAC CTC GGC CGC ACC GGC GAC GAG GCC ACC GGT GTC
his ala val lys val leu asp asp asn leu gly arg thr gly asp glu ala thr gly val
                                            1291/431
1321/441
GCG GTC GTC CGC CGC GCC GTC GAG CCG CTG CGC TGG ATC GCC GAG AAC GCC GGC CTC
ala val val arg arg ala ala val glu pro leu arg trp ile ala glu asn ala gly leu
                    1351/451
1381/461
GAG GGC TAC GTC ATC ACC AAG GTG GCG CTC GAC AAG GGC CAG GGC TTC AAC GCG
glu gly tyr val ile thr lys val ala leu asp lys gly gln gly phe asn ala
                1411/471
1441/481
GCC ACC GGC GAG TAC GGC CAC CTG GTC CAC GGC GTC ATC GAC CCG GTC AAG GTC ACC
ala thr gly glu tyr gly asp leu val lys ala gly val ile asp pro val lys val thr
            1471/491
1501/501
CGC TCC GCC CTG GAG AAC GCG GCC TCC ATC GCC TCC CTG CTG ACG ACC GAG ACC CTG
arg ser ala leu glu asn ala ala ser ile ala ser leu leu thr thr glu thr leu
            1531/511
1561/521
GTC GTC GAG AAG CCG GCC GAG GAG CCC GAG GCC GGT CAC GGT CAC GGG CAC AGC CAC
val val glu lys pro ala glu glu pro glu ala gly his gly his gly his ser his
            1591/531

FIG. 8D

```
          1          10         20         30         40         50         60
   1   CCGGCCGGGC TGAGGTTGGC TGGCTGGCCG GGTTCGGCCG GTGGGTCGAG GTGGGTCGAG GTGGCCTGGC    60
  61   CGGGCTCGCC AGGGTGAGTT GGCCGAGCCG AGGCGGCCG  GGGGCTCCCC GGGGCTCCCC GGGCCGAGTT   120
 121   GGCGCGGCCA GGCCAGGGCT CAGCAGGGTG GGGAGTGGG  GCAGGCGGCC CGGTAGGGGA             180
 181   GTGCGGGAGG GCAGCGGCCG CCCGCGCGCG CCGCGCGCAT TGGCACTCCG CTTGACCGAG TGCTAATCGC   240
 241   GGTCATAGTC TCAGCTCTGG CACTCCCCGC AGGAGAGTGC CAACACAGCG ACGGGCAGGT              300
 301   CCGGCACCCG CGACGACGGA TCGACCTGGT CGCCACACTC AGATCAGTTA ACCCCGTGAT              360
 361   CTCCGAAGGG GGAGGTCGGA TCGTGACGAC CGCCAGCTCC AAGGTTGCCA TCAAGCCGCT              420
 421   CGAGGACCGC ATCGTGGTCC AGCCGCTCGA CGCCGAGCAG ACCACGGCTT CGGGCCTGGT              480
 481   CATCCCGGAC ACCGCGAAGG AGAAGCCCCA GGAGGGCGTC GTCCTCGCGG TCGCCCCGGG              540
 541   CCGCTTCGAG AACGGCGAGC GCTGCCGCT  ACCGGCGACG GAGTACCTCG TCGTGCTGTA              600
 601   CAGCAAGTAC GGCGGCACCG AGTCAAGTA  CAACGGCGAG TCCTCTCGGC                         660
 661   CCGCGACGTT CTCGCCATCA TCGAGAAGTA GCAGGCCGGA CGCGAGCCCG                         720
 721   GACGGCAGAC TCCACCTTTT TCCTGAAGCG CGCCCCTGGC CCCCGCGAGT GTTTGCCGGG              780
 781   TGGCGAGGGG CGCCTTTCAT TTCGAGAGCG CGGCGGCAGG CCGCTCCGAG AGGATTCGAA              840
 841   AAGCTCCCAT GGCGAAGATT CTGAAGTTCG ACGAGGACGC CCGTCGCGCC CTTGAGCGCG              900
 901   GCGTGAACCA GCTGGCCGAC ACCGTCAAGG TGACCATCGG CCCCAAGGGC CGCAACGTCG              960
 961   TCATCGACAA GAAGTTCGGC GCCCGACCA  TCACCAACGA CGGCGTCACC ATCGCCCGTG             1020
1021   AGGTCGAGTG CGACGACCCG TACGAGAACC TCGGCGCCCA GCTCGTCAAG GAGGTGGCGA             1080
1081   CCAAGACCAA CGACATCGCG GGTGACGGCA CCACCACCGC GACCGTGCTG GCCCAGCGCA             1140
1141   TGGTCCGCGA GGGCCTGCGC AACGTCGCC  CCGGCGCCTC CCCGCGCC                          1200
1201   GCATCGACGC CGCCGTCGCC GCCGTCTCCG CCGAGCTGCT CGACACCGCG CGCCCGATCG             1260
1261   ACGACAAGTC CGACATCGCC GCCGTCGCCG CGCTCTCCGC GCAGGACAAG CAGGTCGGGCG            1320
                                    FIG. 9A
```

```
1321  AGCTCATCGC  CGAGGCGATG  GACAAGGTCG  GCAAGGACGG  TGTCATCACC  GTCGAGGAGT  1380
1381  CCAACACCTT  CGGTGTCGAC  CTGGACTTCA  CCGAGGGCAT  GGCCTTCGAC  AAGGGCTACC  1440
1441  TGTCCCCGTA  CATGGTGACC  GACCAGGAGC  GTATGGAGGC  CGTCCTCGAC  GACCCGTACA  1500
1501  TCCTGATCCA  CCAGGCAAG   ATCGGTTCGA  TCCAGGACCT  GCTGCCGCTG  CTGGAGAAGG  1560
1561  TCATCCAGGC  GGGTGGCTCC  AAGCCGCTGC  TGATCATCGC  CGAGGACGTC  GAGGGCGAGG  1620
1621  CCCTGTCGAC  CCTGGTGGTC  AACAAGATCC  GCGGCACGTT  CAACGCCGTC  GCCGTCAAGG  1680
1681  CGCCCGGCTT  CGGTGACCGC  CGCAAGGCGA  TGCTCGGGCGA CATGGCCACC  CTCACCGGTG  1740
1741  CCACCGTCAT  CGCCGAGGAG  GTCGGCCTCA  AGCTCGACCA  GGCCGGTCTG  GACGTGCTGG  1800
1801  GCACCGCCCG  CCGCGTCACC  GTCACCAAGG  ACGACACGAC  CATCGTGGAC  GGCGGCGGCA  1860
1861  ACGCCGAGGA  CGTCCAGGGC  CTCCAGGAGC  AGATCAAGGC  CGAGATCGAG  TCGACCGACT  1920
1921  CGGACTGGGA  CCGCGAGAAG  CTCCAGGAGC  AGCTGAAGGA  GCGCAAGCAC  GGCGTCTGCG  1980
1981  TGATCCGCGT  CGGCGCGGCC  ACCGAGGTCG  AGGAGGGCAT  CGTCTCCGGT  GGTGCTCCG   2040
2041  ACGCCATCTC  CGCGACCCGC  GCCGGGTCCG  GCCGGTCG    CCGCACCGGC  GACGAGGCCA  2100
2101  CGCTGGTCCA  CGCGGTCAAG  GTCCTGGACG  ACAACCTCGG  GCGGCTGGATC  GCCGAGAACG  2160
2161  CCGGTGTCGC  CGCCGTTCCGC  CGCGCCCCG   AGGTGGCGGA  GCTCGACAAG  GGCCAGGGCT  2220
2221  CCGGCCTCGA  GGGCTACGTC  ATCACCACCA  AGGTGCGCGA  GCTCGACAAG  GACCCGGTCA  2280
2281  TCAACGCGGC  CACCGGCGAG  TACGGGCGACC  TGGTCAAGGC  CCTCCATCGC  CTGACGACCG  2340
2341  AGGTCACCCG  CTCGCCCTG   GAGAACGCGG  CCTCCATCGC  CTCCCTGCTC  CTGACGACCG  2400
2401  AGACCCTGGT  CGTCGAGAAG  CGTCGAGAAG  AGGAGCCCGA  GGCCGGTCAC  CTGACGACCG  2460
2461  ACAGCCACTG  AGGCTGACCC  CTTCCGCAGC  CGAGGCCCGG  CTCCCCGTCG  CGGGGAGCCG  2520
2521  GCCCTCCGGC  GTGTCCGGGA  CCCCCGGGA   CGCGCCGACGC CTACCGCGGC  CGTACTTGC   2580
2581  GGCCGGTACG  CGAGGTCATC  CCGGTCAGCA  GGGCCCGCGG  GGTCAGCTTC  ACCAGCCCA   2640
2641  TCAGGCCTT   GTACCGAGGG  TCGGGAT                                        2668

|         |         |         |         |         |
       10        20        30        40        50        60

FIG. 9B
```

REGULATORY NUCLEOTIDE SEQUENCE OF THE INITIATION OF TRANSCRIPTION

This application is a divisional of U.S. application Ser. No. 08/461,775, filed Jun. 5, 1995 now U.S. Pat. No. 5,858,773, which is a continuation of U.S. application Ser. No. 08/050,313, filed May 10, 1993, now abandoned, which is a 371 of PCT/FR91/00701, filed Sep. 3, 1991.

BACKGROUND OF THE INVENTION (i) Field of the Invention

The invention relates to a regulatory nucleotide sequence of the initiation of transcription and its use in the production of polypeptides by the recombinant approach.

The technical problem which presented itself when the present invention was being developed was to identify a strong and, if possible, thermoinducible promoter, which could be used in a large number of micro-organisms and, in particular, in the Actinomycetes.

(ii) Description of the Prior Art

The Actinomycetes constitute a bacterial order of great economic and medical importance, mention needs only to be made of the fact that the Actinomycetes include, in particular, the Streptomyces and Mycobacterium genera.

The Streptomyces are used for the production of about 70% of the antibiotics sold today; furthermore, even though there is no longer occasion to describe the ravages caused by *Mycobacterium tuberculosis* and *Mycobacterium leprae*, great interest is attached to the expression of the heterologous antigen in a strain of *M. bovis* BCG in order to produce a living polyvalent strain to be used as a vaccine.

The genetics of these bacteria has been lie studied at the molecular level, but the regulation of genetic expression seems to be different from that which has been described for bacteria which have been studied in more detail such as *Escherichia coli* or *Bacillus subtilis.*

In particular, the Actinomycetes , the DNA of which is rich in G+C, recognize the "promoter" sequences in *Escherichia coli* and *Bacillus subtilis*, poorly or not at all. Baird et al. (J.Gen.Microbiol.1989, 135, 931–939) studied the genes coding for heat shock proteins in Mycobacterium and postulated that two sequences, TTGAG and TCTCATGT, located upstream from the sequence coding for the heat shock protein of 10 kDA of *Mycobacterium tuberculosis*, constitute the −35 and −10 regions of the promoter.

In fact, the two sequences exhibit a high degree of homolgy with the consensus sequence of the promoter in *E. coli*. Furthermore, sequences located upstream from the genes coding for other heat shock proteins in various species of Mycobacterium (for example, the protein of 65 kDa of *Mycobacterium leprae* or that of 64 kDA in *M. bovis*also contain a couple of sequences of the same type, i.e.: TTGCCG and TTTCAT, or TTGCCG and CTTCAT, and which thus show a high degree of homology with the *E. coli* promoter and with the "−35 and −10" sequences of the 10 kDa species of *Mycobacterium tuberculosis.*

Acccording to that article and the one by Thole et al. (Infection and Immunity, 55, 1987, 1466–1475), the promoters responsible for the transcription of the genes of the heat shock proteins in Mycobacterium contain, as −35 and −10 sequences, this type of coupled sequences.These sequences will be designated subsequently as "−10 and −35 sequences of the *E. coli* type". This being so, the authors had not confirmed this hypothesis by mapping and the identity of the promoters consequently remains uncertain.

In a surprising manner, the present inventors have noticed that the −10 and −35 sequences of the *E. coli* type are also present in Streptomyces, but do not play a role in the initiation of the transcription of heat shock proteins in the bacteria of this genus. It should be noted that, in the articles mentioned above, Baird and Thole had also observed the presence, in sequences upstream from the genes coding for the heat shock proteins in Mycobacterium, a palindromic motif containing the sequence GCACTC 9N (SEQ ID NO:1) GAGTGC.However, the precise role of this motif had not been identified. Thole postulates that this motif is implicated either in the termination of transcription of an operon located upstream from the gene coding for the heat shock protein or in the regulation of the translation of a polycistronic messenger.

With the aim of cloning a strong (and, if possible, thermoinducible) promoter, which can be used in a large number of Actinomycetes, the inventors have studied the response to heat shock in Streptomyces and have cloned a strongly expressed protein in order to characterize its promoter.In fact, the response phenomenon to heat shock resulting in the de novo of proteins is a universal phenomenon; it may thus be anticipated that its regulation will be similar in various Actinomycetes and in particular that the promoters will have consensus sequences which will enable them to be used in a large number of strains.

SUMMARY OF THE INVENTION

The inventors have thus identified and characterized two functional promoters in the Streptomyces and, in addition, have been able to identify the function of the said palindrome as a consequence of the observation that each of these promoters contains the motif (SEQ ID NO:1) GCACTC 9N GAGTGC.

The invention relates to a recombinant nucleotide sequence characterized in that it comprises:

- a regulatory sequence of the initiation of transcription, this regulatory sequence containing a promoter in combination with the motif (SEQ ID NO:1) GCACTC 9N GAGTGC in which "N" signifies any one of the 4 bases: thymine, guanine, adenine and cytosine;
- a sequence coding for a polypeptide, called "heterologous polypeptide", other than that naturally associated with the said promoter, the said coding sequence being positioned downstream from the said regulatory sequence of the initiation of transcription at a site which, under suitable conditions, would permit the polypeptide under the control of the said promoter to be expressed. The recombinant nucleotide sequence of the invention is capable of giving rise to the expression of a heterologous gene in a cell containing it .

The regulatory sequence of the initiation of transcription, which forms part of the recombinant nucleotide sequence , is composed of a promoter in association with the motif (SEQ ID NO:1) GCACTC 9N GAGTGC.In this context, "in association" means that themotif (SEQ ID NO:1) GCACTC 9N GAGTGC may be distinct from the promoter or it may be contained, at least in part, within the promoter. This latter possibility includes the situation in which the motif overlaps the promoter sequence and the situation in which the motif constitutes an integral part of the promoter.

Promoters associated with the sequence (SEQ ID NO:1) GCACTC 9N GAGTGC which are particularly preferred according to the invention are the promoters present in the Actinomycetes and, more particularly, those which in the bacterial genome are normally associated with heat shock proteins. As examples of this type of promoter, mention may be made of the promoters of heat shock proteins of 18 kDA (P1) and 56 kDa (2) in *Streptomyces albus* identified within the framework of the invention by the inventors: P1 corresponding to one of the sequences (SEQ ID NOS: 2–3):

```
5' GGAGGCCCCTAGCGCCTGCACTCTCCTACCCCGAGTGCTATTATTGGCGT

3' TA
``` or

```
5' GGAGGCCCCTAGCGCCTGCACTCTCCTACCCCGAGTGCTAATTATTGGCG

3' TTA
```

P2 corresponding to one of the sequences (SEQ ID NOS: 4–5):

```
5' GGAGGCCCCTAGCGCCTGCACTCTCCTACCCCGAGTGCTATTATTGGCGT

3' TA
``` or

```
5' GGAGGCCCCTAGCGCCTGCACTCTCCTACCCCGAGTGCTAATTATTGGCG

3' TTA
```

Each of these promoters may be shortened by a maximum of 4 or 5 bases at the 5' end without adversely affecting its activity. Other types of promoters are those for heat shock proteins of 10 kDa and 65 kDa from *Mycobacterium tuberculosis*, 64 kDa from *M. bovis* and 65 kDa from *M. leprae*.

The association of the GCACTC 9N GAGTGC motif with the promoter confers thermoinducible character on the promoter. It is probable that this sequence is an operator and constitutes the binding site for a repressor, which thus prevents the RNA polymerase from binding to the −10 and −35 sequences of the promoter.

In the case in which the motif is distinct from the promoter, it is preferably upstream from the promoter, by about 150 to 200 bases, for example.

The recombinant sequence of the invention contains, in addition, to the regulatory sequence of the initiation of transcription, a sequence coding for a polypeptide called "heterologous polypeptide", different from that which is naturally associated with the said promoter. Thus, the immediate genetic environment of the promoter is different from that in the genome from which it is derived As examples of types of heterologous polypeptides, mention may be made of neutralizing antigens which can be used in the production of recombinant live vaccines or polypeptides conferring resistance to an antbiotic, enzymes, etc. . . .

In the nucleotide sequence of the invention, the coding sequence is positioned downstream from the said regulatory sequence. Their relative positions are, of course such that the expression of the coding sequence takes place under the control of the promoter.

In addition, the invention relates to an expression vector containing the nucleotide sequence of the invention, for example a plasmid.

The invention also relates to a cell transformed by this expression vector, the said cell being capable of recognizing the promoter used in the regulatory sequence of the initiation of transcription. The transformed cells are preferably prokaryotic cells and, more particularly, prokaryotes belonging to the order of the Actinomycetes, for example Streptomyces or Mycobacterium.

The invention also relates to a procedure for the production of a polypeptide characterized in that it composes the following steps:

transformation of a cell by an expression vector according to the invention under conditions allowing the expression of the said polypeptide, the said cell being capable of recognizing the said promoter;

recovery of the polypeptide expressed.

The conditions allowing the expression of the polypeptide are those known from the prior art and, in the present case, preferably include the use of heat shock, which has the effect of inducing expression. The heat shock may be an increase in temperature from about 37° C. to 45° C. or, in particular, 40° C. to 45° C, for example 37° C. or 41° C. in Streptomyces, 42° C. to 45° C. in the case of Mycobacterium.

It is interesting to note that the use of the promoters P1 and P2 of the invention results in a sustained expression of the heterologous protein at high temperature, for example between 37° and 41° C. in Streptomyces.

Another feature of the invention relates to the possibility of transforming a promoter into a thermoinducible promoter as a result of its association with the (SEQ ID NO:1) GCACTC 9N GAGTGC motif. More particularly, this feature of the invention relates to a procedure for conferring a thermoinducible character on a promoter, characterized by the juxtaposition of a sequence containing the (SEQ ID NO:1) GCACTC 9N GAGTGC motif, on the one hand, and the promoter, on the other, the sequence containing the (SEQ ID NO:1) GCACTC 9N GAGTGC motif being positioned upstream from the promoter, or by insertion of the sequence containing the (SEQ ID NO:1) GCACTC 9N GAGTGC motif at a site which is, at least in part, contained within the promoter, this later site being selected such that the simple insertion of the said palindrome does not pet the activity of the promoter. The precise position in which the (SEQ ID NO:1) GAGTGC 9N GAGTGC motif must be placed with respect to the promoter in order to be able to confer thermoinducible character may vary depending on the promoter used This can be checked by detecting, on application of a heat shock, the expression of an easily detectable heterologous gene, for example a gene marker such as LacZ, in a cell transformed by the construction under test. The positioning of the (SEQ ID NO:1) GCACTC 9N GAGTGC motif at a site about 150 to 200 bases upstream from the promoter can confer this thermoinducible character. In some cases, the (SEQ ID NO:1) GCACTC 9N GAGTGC motif may be inserted at a site which is, at least in part, contained within the promoter. In such a case, the insertion site must be selected such that the simple insertion of the motif does not perturb the activity of the promoter other than that due to the introduction of the thermoinducible effect. It is important not to modify the −10 and −35 sequences of the promoter when this insertion is made. The thermoinducible character of the regulatory sequence of the initiation of transcription thus produced may be checked by applying the method described above.

While they were studying the promoters, the inventors studied the response to heat shock of various species of Streptomyces. In addition to the principal heat shock proteins with molecular weights of 90–100, 70 and 56–58 kDa, a protein of 16 to 18 kDa was observed in each of the species tested. This protein (called HSP18) is produced at very high levels in Streptomyces albus when the culture is transferred from 30° to 37° C. and may constitute up to 10% of the total proteins. The induction by means of heat shock of the proteins of 70 and 90–100 kDa is transient, whereas that of the proteins of 56–58 kDa and 18 kDa is constitutive, the production being sustained at high temperatures.

The protein called HSP18 was purified and characerized. Its properties are unlike those of other heat shock proteins. For example, apart from its relatively small size and its being regulated constitutively at high temperature, it possesses an isoelectric point higher than 9. This very high isoelectric point is, however, not reflected in its amino acid composition (see Table 2).

Furthermore, the determination of its amino acid composition revealed a rather low methionine content, which is not consistent with the results of /35S/ methionine incorporation experiments (see Table 1). These observations suggest that the HSP18 protein undergoes modification which takes place after translation.

The HSP18 protein does not react with polyclonal antibodies against the GroEL protein from *E. coli*, nor with monoclonal antibodies specific for the 65 kDa heat shock protein from *Mycobacterium leprae*.

A study of the transcription of the "groEL-1" gene coding for the HSP18 protein showed that HSP18 is, in fact, a truncated protein. The groEL-1 gene codes in reality for a protein of 56 kDa which is modified after translation and gives rise to the 18 kDa protein.

FIG. 6 shows the partial sequence of the groEL-1 gene and its amino acid translation product. This sequence corroborates the sequences determined by Edman degradation of HSP18. The sequence shown in FIG. 6 lacks the COOH terminus of the 56 kDa protein. The sequence of the 18 kDa protein is included in this parent sequence, their two NH2 termini being identical (amino acid No. 1). HSP18 extends maximally upto about amino acid 170.

FIG. 8 gives the complete sequence of the protein encoded by the groEL-1 gene, which comprises the HSP18 protein, just like the figure shown in FIG. 6. The invention relates to a heat shock protein comprising either (i) the amino acid sequence shown in FIG. 6 or the sequence corresponding to the amino acid sequence shown in FIG. 8, or (ii) a sequence exhibiting at least 85% homology with this sequence, or (iii) a part of the sequence (i) or (ii) comprising the NH2 terminus and extending up to about amino acid 170, the polypeptide (iii) having a molecular weight of about 18 kDa and a very basic isoelectric point of about 9.

By analogy with the function of other proteins of the GroEL type, it is probable that HSP 18 is essential for the survival of the cell and plays a role of "molecular chaperon", i.e. binds transiently to nascent polypeptides preventing the aggregation of insoluble proteins and making folding and transport through the cell membrane possible. It is also possible that HSP18 is implicated in the resistance of the strain to its own antibiotics or in tolerance to heat In accordance with a special feature, the invention also relates to a polypeptide containing the COOH terminal region of the GroEL-1 protein as shown in FIG. 8A particular polypeptide corresponding to this definition contains or corresponds to the following amino acid sequence: Gly His Gly His Gly His Ser His.

The amino acid sequence described above corresponds to an original sequence of amino acids when compared with the COOH terminal peptide sequences known for heat shock proteins. This COOH terminal sequence might be implicated in the formation of the truncated 18 kDa protein.

BRIEF DESCRIPTION OF THE DRAWINGS

Various features of the invention are illustrated in the figures:

FIG. 2 (SEQ ID NO:1–6) shows the P2 promoter of groEL-2 and the P1 promoter of groES and groEL- 1.

FIG. 5 (SEQ ID NO:7) shows the nucleotide sequence and the amino acid sequence deduced from the groES structural gene and the GroES protein.

FIG. 6A–C (SEQ ID NO:8) illustrate the nucleotide sequence as well as the deduced amino acid sequence of the protein precursor of HSP18.

FIG. 7A–B (SEQ ID NO:9) show the nucleotide sequence of the gro es el operon together with its promoter sequence.

FIG. 8A–D (SEQ ID NO:10) show the complete amino acid sequence encoded by the groEL-1 gene with which it is aligned.

FIG. 9A–B (SEQ ID NO:11) show the nucleotide sequence of the complete groEL-1 gene.

DETAILED DESCRIPTION OF PREFERRED EMBODIMENTS

EXAMPLES

Figure 1:
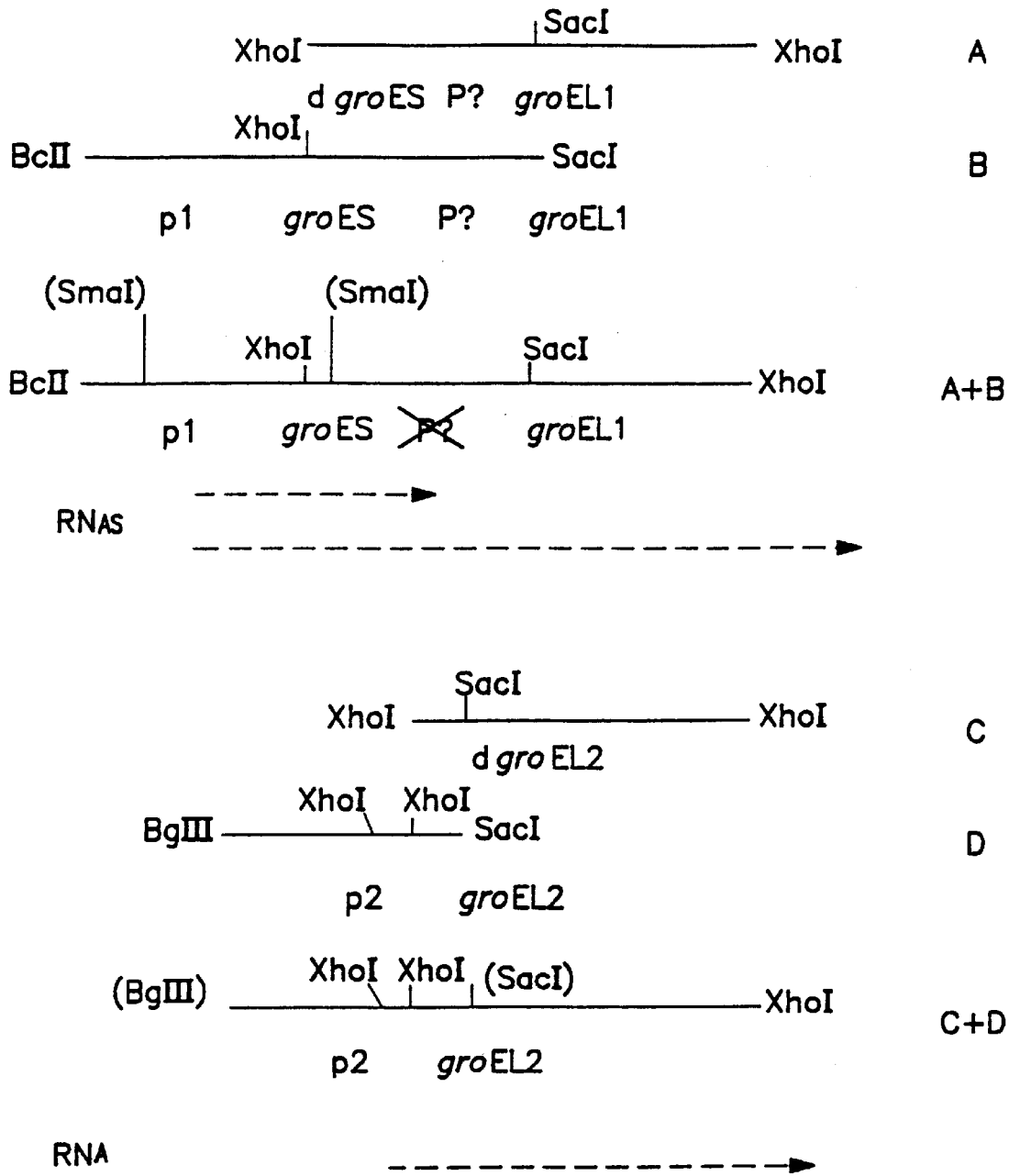
FIG. 1 shows schematically the cloning of the groEL-1, groES and groEL-2 genes. The sites which have served for the construction of the plasmids pPM1005 and pPM997+ Neo are shown in brackets.

Effect of temperature on protein synthesis in Streptomyces:

The total protein extracts of 15 different species of Streptomyces were prepared before and after application of a heat shock (increase in temperature from 30° C. to 41° C.). Major heat shock proteins of 90–100, 70 and 56–58 kDa were detected on a SDS-PAGE gel, stained with Coomassie blue. In addition, a molecular band corresponding to a protein of 18 kDa was also observed in some species This protein was very strongly induced in *Streptomyces albus*.

Immunological properties of the proteins

A "Western blot" analysis of the proteins on the gel with monoclonal antibodies against the 65 kDa heat shock protein of *Mycobacterium leprae* and with polyclonal antibodies against the GroEL protein of *E. coli* was carried out. None of the proteins reacted with the monoclonal antibodies and only the 56–58 kDa HSPs reacted with the polyclonal antibodies.

Study of the heat shock proteins in *Streptomyces albus:*

The response to heat shock in Streptomyces albus was analysed by means of electrophoresis of the total proteins at 30° C. and 41° C. The proteins were labelled for 40 minutes. The amino acids used were /35S/ methionine and /14C/ alanine. It was possible to visualise four major heat shock proteins. HSP90, which could not be detected at 30° C., represented about 3% of the total proteins after heat shock- .The amount of HSP70 was at least doubled.HSP56-58 showed an increase of 30% and HSP18, which could not be detected before heat shock, represented 4 to 7% of the total proteins after the shock (see Table 1).

TABLE 1

QUANTIFICATION OF THE LEVELS OF SYNTHESIS OF THE MAJOR HEAT SHOCK PROTEINS AFTER LABELLING WITH 14C ALANINE AND 35S METHIONINE
Level of synthesis (a) at 30° C. and 41° C.

| Protein MW(b) | 35S/30° C. | 35S/41° C. | 14C/30° C. | 14C/41° C. |
|---|---|---|---|---|
| 90 | c | 3 | — | 2.9 |
| 70 | 2.7 | 6.4 | 2.3 | 5.8 |
| 56–58 | 6.8 | 8.4 | 6.2 | 9.0 |
| 18 | >0.7? | 6.9 | >0.7? | 3.8 | a. expressed as a percentage of the total optical density (O.D.) measured by means of autoradiography.
b. apparent molecular weight in kDA.
c. not detected.

Study of HSP18 of *Streptomyces albus*:

The 18 kDa protein of *Streptomyces albus* (HSP18), which is extremely basic, was purified and its partial amino acid composition was determined (see Table 2):

TABLE 2

AMINO ACID COMPOSITION OF HSP18

| Asx | 12.2 |
|---|---|
| Thr | 9.4 |
| Ser | 3.2 |
| Glx | 10.8 |
| Ala | 12.1 |
| Cys | 0.0 |
| Met | 0.0 |
| Val | 9.2 |
| Ile | 5.7 |
| Leu | 6.8 |
| Tyr | 1.3 |
| Phe | 1.9 |
| His | 0.3 |
| Lys | 6.9 |
| Arg | 4.5 |
| Gly | 11.0 |
| Pro | 4.4 |

The sequence of the NH2 terminus and of two internal fragments of the protein were determined by means of Edman degradation Synthesis of oligonucleotides:

Two degenerate nucleotide probes of 30 bases were synthesized on the basis of the peptide sequence of one of the internal fragments described above.The sequence of this fragment (SEQ ID NO:12) is:

... D - D - P - Y - E - N - L - G - A- Q . . .

The following (SEQ ID NO: 13–14) deoxyoligonucle-otide probes were synthesized

```
5' GAC-GAC-CCC-TAC-GAG-AAC-CTG-GGC-GCC-CA 3'OL1
        G            C        T

3' CTG-CTG-GGG-ATG-CTC-TTG-GAC-CCG-CGG-GTC 5'OL2
        C            G        A
```

Cloning of the gene for the thermoinducible protein HSP18:

After hybridization at 60° C. in 5xSSC, these oligonucle-otide probes have made it possible to characterize and clone a 1.9 kb Xhol resummon fragment of *Streptomyces albus* (see cloning A in FIG. 1).

This fragment was sequenced ; it contains an open reading frame which extends from an ATG at position 430 to beyond the cloned region thus coding for a protein of more than 50 kDa, but the NH2 terminus of which corresponds to the nucleotide sequence deduced from the peptide sequence of HSP18.The amino acid sequence corresponding to this gene shows, in addition, a strong homology throughout its length with the heat-shock protein groEL of *E. coli* and the 65 kDa protein from *Mycobacterium leprae* (75% homology) .Initially, this gene was called "groEL-b 1".

Demonstration and cloning of a second "groEL-like" gene in *Streptomyces albus:*

Hybridizations of the genome of Streptomyces albus were carried out using the 5' part of the gene for HSP65 of *Mycobacterium leprae* as probe; this probe gives two signals after hybridization with the genome of *Streptomyces albus,* one strong and one weak, irrespective of the enzyme used to digest the DNA.The weak signal corresponds to the signals obtained with the oligonucleotides deduced from HSP18, i.e. to the groEL-1 gene.The strong signal corresponds to a gene coding for another "GroEL-like" protein of accepted size (65 kDa).There are thus two groEL-like genes in *Streptomyces albus.*

Cloning of the gene for the heat-shock protein HSP65 of *Streptomyces albus:*

The 1.2 kb Xhol restriction fragment strongly bound by the HSP65 probe from *Mycobacterium leprae* was cloned (cloning C in FIG. 1).

The nucleotide sequence of this fragment was determined The 1 2 kb Xhol fragment codes for an internal fragment of a protein showing 90% homology with the 65 kDa protein from *Mycobacterium leprae*, in addition the two "groEL-like" genes 1 and 2 in *Streptomyces albus* show an 80% homology.

The gene coding for this 65 Da protein was called groEL-2.

Study of the transcription of the "groEL-like" genes and the search for the promoters:

The total RNAs of the *Streptomyces albus* strain were extracted at various times during a heat shock experiment and treated according to the "Northern blot" technique, then hybridized with various oligonucleotides, the synthesis of which was based on either the groEL-1 sequence or the groEL-2 sequence and which were specific for each of the regions selected in these two sequences.The same nitrocel-lulose filters were used in repeat hybridizations with the totality of the two cloned fragments.Three very strongly thermoinducible transcripts are observed; their sizes are about 2500,2100 and 650 bases, respectively.The one with 2100 bases corresponds to the groEL-2 transcript, the one with 650 bases to the transcript of the gene situated upstream from groEL-1; the one with 2500 bases to the co-transcription of groEL-1 and the gene situated upstream from groEL-1.These results showed, on the one hand, that the two genes groEL-1 and groEL-2 had indeed strong and inducible promoters, in particular thermoinducible promoters, and, on the other, that the groEL-1 promoter had not been cloned in the 1.9 kb fragment.In particular, these results show that none of the RNAs starts at the loop marked P? in FIG. 1, the sequence postulated as being capable of serving as promoter in Mycobacterium.

In fact, this loop contains two sequences ,TTTGCCGGG and TTTCAT, which , in the absence of mapping data for thepromoter, were considered to be the −35 and −10 regions, respectively, of the promoter for the 65 kDa protein from Mycobacterium (see, for example, J.Gen.Microbiol. (1989), 135, 931–939).These results show that these two sequences do not form part of the promoter of the groEL-1 gene in *Streptomyces albus*.

The desired promoter would be expected to be situated upstream from the gene forming an operon with groEL-1. The gene situated upstream from groEL-1 has been identified; it is a gene showing strong homology to the groES gene of *E. coli* where it also forms an operon with groEL-1 (see FIG. 5).

Cloning of the promoter regions of the two genes groEL-1 and groEL-2:

Two novel fragments of *Streptomyces albus* DNA, hydrolysed by BclI/SacI (1700 bp) and BglII/SAcI (900 bp), were cloned with the aid of oligonucleotides synthesized starting from the sequence of the previously cloned fragments and described above. Hence they partially span the fragment beating groEL-1 and that bearing groEL-2, respectively and extend upstream for about 800 bp in each case (clonings B and D in FIG. 1).

These fragments were sequenced, then the promoters were characterized by means of mapping using the S1 nuclease and by primer extension using the reverse transcriptase. The sequences of the promoters of the two genes groEL-1 and groEL-2 thus characterized are not identical (FIG. 2), but they show considerable structural homology, in particular both possess the following palindromic sequence:

GCACTC 9N GAGTGC

The sequences of the two promoters are the following:

P1 corresponding to one of the sequences (SEQ ID NOS 2–3):

```
CATTGGCACTCCGCTTGACCGAGTGCTAATCGCGGTCATAGTCTCAGCTC
5'

TG
3'
``` or

```
GCATTGGCACTCCGCTTGACCGAGTGCTAATCGCGGTCATAGTCTCAGCT
5'

CTG
 3'
```

P2 corresponding to one of the sequences (SEQ ID NOS:4–5):

```
GGAGGCCCCTAGCGCCTGCACTCTCCTACCCCGAGTGCTATTATTGGCGT
5'

TA
3'
``` or

```
GGAGGCCCCTAGCGCCTGCACTCTCCTACCCCGAGTGCTAATTATTGGCG
5'

TTA
 3'
```

Figure 3:
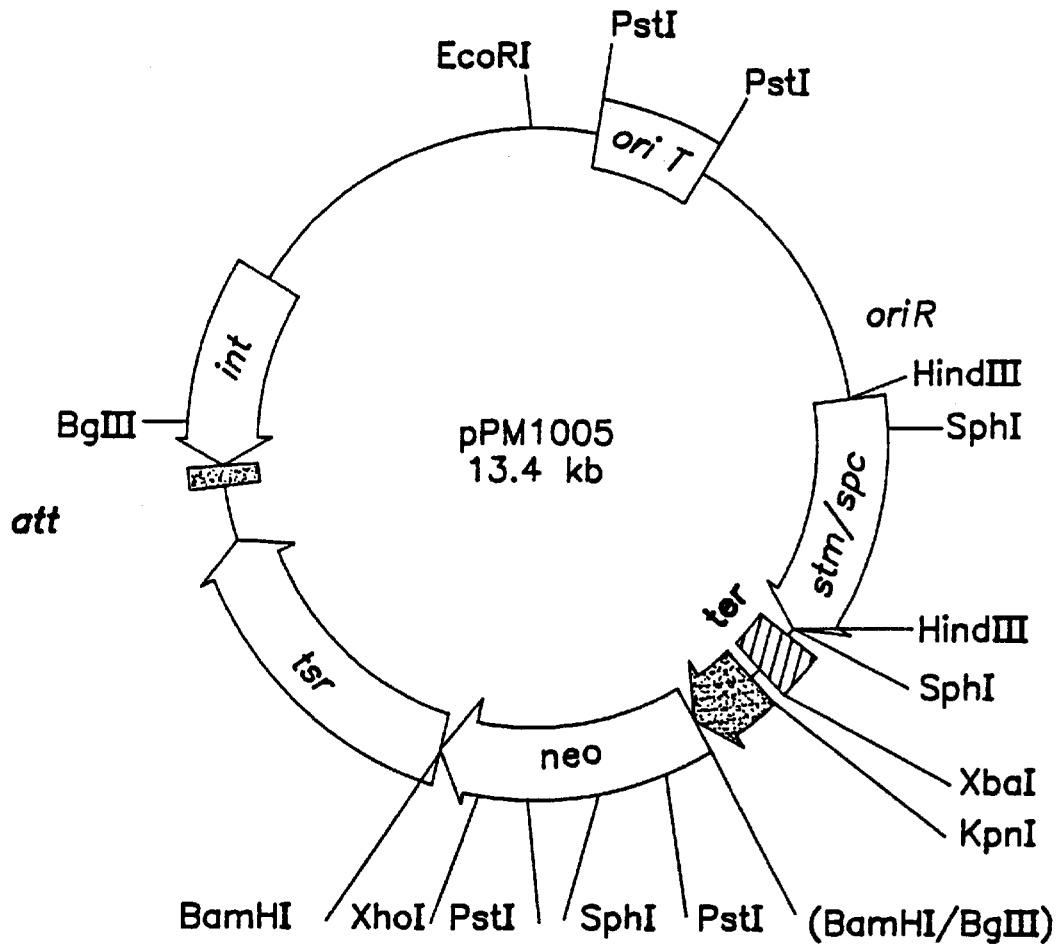
FIG. 3 shows the vector pPM1005 containing the neo gene of TN5 under the control of the SmaI fragment of 440 bp of *Streptomyces albus*. This fragment contains the P1 promoter and the fir 160 base pairs of the groES gene.
Figure 4:
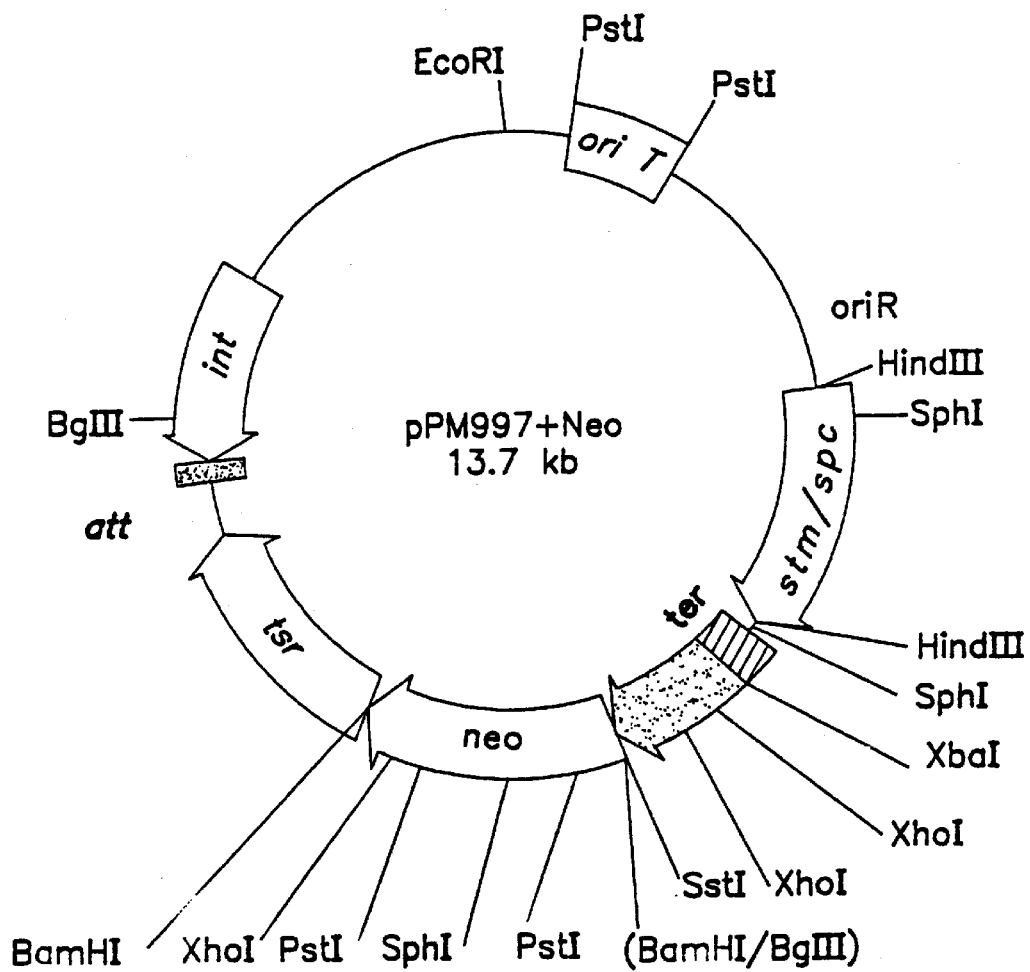
FIG. 4 shows the vector pPM997+Neo containing the neo gene of Tn5 under the control of the BglII/SstI fragment of 800 bp of *Streptomyces albus*. This fragment contains the P2 promoter and the first 183 bp of the groEL-2 gene.

Use of the promoters of groEL-1 and groEL-2 for the expression of a heterologous gene:

These two promoters were used for the expression of the heterologous neo gene of the transposon Tn5 of Klebsiella. This gene codes for an aminoglycoside phosphotransferase (APH) which confers resistance to neomycin/kanamycin. This gene was cloned downstream from the two promoters (FIGS. 3 and 4), then introduced into *Streptomyces albus* and also into *S. lividans*. The neo gene is then strongly expressed, as is shown by the considerable degree of resistance to these antibiotics which it confers; furthermore, we have been able to visualize the synthesis of the APH in crude extracts after electrophoresis on polyacrylamide gel and immuno-blotting with anti-APH antibodies. It must be emphasized that these results were obtained in Streptomyces with an integrating vector. Hence, in these experiments, there is only one copy of the neo gene and of the promoter under study per genome. In fact, in order to judge the such of the promoter, it was important not to increase the expression of neo artificially by increasing the number of copies of it by using a vector which generates a large number of copies.

The HindIII-BamII fragments of pPM10 5 and the SmaI-SmaI fragments of pPM997 have also been inserted into Mycobacterium. The SmaI-SmaI fragment of pPM997 contains the neo gene, the P2 promoter and the terminator.

---

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GCACTCNNNN NNNNNGAGTG C                                                           21

(2) INFORMATION FOR SEQ ID NO:2:

(i) SEQUENCE CHARACTERISTICS:
    (A) LENGTH: 52 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:2:

CATTGGCACT CCGCTTGACC GAGTGCTAAT CGCGGTCATA GTCTCAGCTC TG                52

(2) INFORMATION FOR SEQ ID NO:3:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCATTGGCAC TCCGCTTGAC CGAGTGCTAA TCGCGGTCAT AGTCTCAGCT CTG               53

(2) INFORMATION FOR SEQ ID NO:4:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGAGGCCCCT AGCGCCTGCA CTCTCCTACC CCGAGTGCTA TTATTGGCGT TA                52

(2) INFORMATION FOR SEQ ID NO:5:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGAGGCCCCT AGCGCCTGCA CTCTCCTACC CCGAGTGCTA ATTATTGGCG TTA               53

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCACTCNNNN NNNCCGAGTG CTAAT                                              25

(2) INFORMATION FOR SEQ ID NO:7:

(i) SEQUENCE CHARACTERISTICS:
        (A) LENGTH: 309 base pairs
        (B) TYPE: nucleic acid

```
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..306

(xi) SEQUENCE DESCRIPTION: SEQ ID NO:7:

GTG ACG ACC GCC AGC TCC AAG GTT GCC ATC AAG CCG CTC GAG GAC CGC        48
Val Thr Thr Ala Ser Ser Lys Val Ala Ile Lys Pro Leu Glu Asp Arg
 1               5                  10                  15

ATC GTG GTC CAG CCG CTC GAC GCC GAG CAG ACC ACG GCT TCG GGC CTG        96
Ile Val Val Gln Pro Leu Asp Ala Glu Gln Thr Thr Ala Ser Gly Leu
             20                  25                  30

GTC ATC CCG GAC ACC GCG AAG GAG AAG CCC CAG GAG GGC GTC GTC CTC       144
Val Ile Pro Asp Thr Ala Lys Glu Lys Pro Gln Glu Gly Val Val Leu
         35                  40                  45

GCG GTC GGC CCG GGC CGC TTC GAG AAC GGC GAG CGC CTG CCG CTC GAC       192
Ala Val Gly Pro Gly Arg Phe Glu Asn Gly Glu Arg Leu Pro Leu Asp
     50                  55                  60

GTC AAG ACC GGC GAC GTC GTG CTG TAC AGC AAG TAC GGC GGC ACC GAG       240
Val Lys Thr Gly Asp Val Val Leu Tyr Ser Lys Tyr Gly Gly Thr Glu
 65                  70                  75                  80

GTC AAG TAC AAC GGC GAG GAG TAC CTC GTC CTC TCG GCC CGC GAC GTT       288
Val Lys Tyr Asn Gly Glu Glu Tyr Leu Val Leu Ser Ala Arg Asp Val
                 85                  90                  95

CTC GCC ATC ATC GAG AAG TAG                                           309
Leu Ala Ile Ile Glu Lys
                100

(2) INFORMATION FOR SEQ ID NO:8:

(i) SEQUENCE CHARACTERISTICS:
        (A) LENGTH: 1320 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1320

(xi) SEQUENCE DESCRIPTION: SEQ ID NO:8:

ATG GCG AAG ATT CTG AAG TTC GAC GAG GAC GCC CGT CGC GCC CTT GAG        48
Met Ala Lys Ile Leu Lys Phe Asp Glu Asp Ala Arg Arg Ala Leu Glu
 1               5                  10                  15

CGC GGC GTG AAC CAG CTG GCC GAC ACC GTC AAG GTG ACC ATC GGC CCC        96
Arg Gly Val Asn Gln Leu Ala Asp Thr Val Lys Val Thr Ile Gly Pro
             20                  25                  30

AAG GGC CGC AAC GTC GTC ATC GAC AAG AAG TTC GGC GCC CCG ACC ATC       144
Lys Gly Arg Asn Val Val Ile Asp Lys Lys Phe Gly Ala Pro Thr Ile
         35                  40                  45

ACC AAC GAC GGC GTC ACC ATC GCC CGT GAG GTC GAG TGC GAC GAC CCG       192
Thr Asn Asp Gly Val Thr Ile Ala Arg Glu Val Glu Cys Asp Asp Pro
     50                  55                  60

TAC GAG AAC CTC GGC GCC CAG CTC GTC AAG GAG GTG GCG ACC AAG ACC       240
Tyr Glu Asn Leu Gly Ala Gln Leu Val Lys Glu Val Ala Thr Lys Thr
 65                  70                  75                  80

AAC GAC ATC GCG GGT GAC GGC ACC ACC ACC GCG ACC GTG CTG GCC CAG       288
Asn Asp Ile Ala Gly Asp Gly Thr Thr Thr Ala Thr Val Leu Ala Gln
                 85                  90                  95
```

```
GCG CTG GTC CGC GAG GGC CTG CGC AAC GTC GCC GCC GGC GCC TCC CCG      336
Ala Leu Val Arg Glu Gly Leu Arg Asn Val Ala Ala Gly Ala Ser Pro
            100                 105                 110

GCC GCC CTG AAG AAG GGC ATC GAC GCC GCC GTC GCC GCC GTC TCC GCC      384
Ala Ala Leu Lys Lys Gly Ile Asp Ala Ala Val Ala Ala Val Ser Ala
                115                 120                 125

GAG CTG CTC GAC ACC GCG CGC CCG ATC GAC GAC AAG TCC GAC ATC GCC      432
Glu Leu Leu Asp Thr Ala Arg Pro Ile Asp Asp Lys Ser Asp Ile Ala
        130                 135                 140

GCC GTC GCC GCG CTC TCC GCG CAG GAC AAG CAG GTC GGC GAG CTC ATC      480
Ala Val Ala Ala Leu Ser Ala Gln Asp Lys Gln Val Gly Glu Leu Ile
145                 150                 155                 160

GCC GAG GCG ATG GAC AAG GTC GGC AAG GAC GGT GTC ATC ACC GTC GAG      528
Ala Glu Ala Met Asp Lys Val Gly Lys Asp Gly Val Ile Thr Val Glu
                165                 170                 175

GAG TCC AAC ACC TTC GGT GTC GAC CTG GAC TTC ACC GAG GGC ATG GCC      576
Glu Ser Asn Thr Phe Gly Val Asp Leu Asp Phe Thr Glu Gly Met Ala
        180                 185                 190

TTC GAC AAG GGC TAC CTG TCC CCG TAC ATG GTG ACC GAC CAG GAG CGT      624
Phe Asp Lys Gly Tyr Leu Ser Pro Tyr Met Val Thr Asp Gln Glu Arg
    195                 200                 205

ATG GAG GCC GTC CTC GAC GAC CCG TAC ATC CTG ATC CAC CAG GGC AAG      672
Met Glu Ala Val Leu Asp Asp Pro Tyr Ile Leu Ile His Gln Gly Lys
        210                 215                 220

ATC GGT TCG ATC CAG GAC CTG CTG CCG CTG CTG GAG AAG GTC ATC CAG      720
Ile Gly Ser Ile Gln Asp Leu Leu Pro Leu Leu Glu Lys Val Ile Gln
225                 230                 235                 240

GCG GGT GGC TCC AAG CCG CTG CTG ATC ATC GCC GAG GAC GTC GAG GGC      768
Ala Gly Gly Ser Lys Pro Leu Leu Ile Ile Ala Glu Asp Val Glu Gly
                245                 250                 255

GAG GCC CTG TCG ACC CTG GTG GTC AAC AAG ATC CGC GGC ACG TTC AAC      816
Glu Ala Leu Ser Thr Leu Val Val Asn Lys Ile Arg Gly Thr Phe Asn
        260                 265                 270

GCC GTC GCC GTC AAG GCG CCC GGC TTC GGT GAC CGC CGC AAG GCG ATG      864
Ala Val Ala Val Lys Ala Pro Gly Phe Gly Asp Arg Arg Lys Ala Met
    275                 280                 285

CTC GGC GAC ATG GCC ACC CTC ACC GGT GCC ACC GTC ATC GCC GAG GAG      912
Leu Gly Asp Met Ala Thr Leu Thr Gly Ala Thr Val Ile Ala Glu Glu
        290                 295                 300

GTC GGC CTC AAG CTC GAC CAG GCC GGT CTG GAC GTG CTG GGC ACC GCC      960
Val Gly Leu Lys Leu Asp Gln Ala Gly Leu Asp Val Leu Gly Thr Ala
305                 310                 315                 320

CGC CGC GTC ACC GTC ACC AAG GAC GAC ACG ACC ATC GTG GAC GGC GGC     1008
Arg Arg Val Thr Val Thr Lys Asp Asp Thr Thr Ile Val Asp Gly Gly
                325                 330                 335

GGC AAC GCC GAG GAC GTC CAG GGC CGC GTC GCC CAG ATC AAG GCC GAG     1056
Gly Asn Ala Glu Asp Val Gln Gly Arg Val Ala Gln Ile Lys Ala Glu
        340                 345                 350

ATC GAG TCG ACC GAC TCG GAC TGG GAC CGC GAG AAG CTC CAG GAG CGC     1104
Ile Glu Ser Thr Asp Ser Asp Trp Asp Arg Glu Lys Leu Gln Glu Arg
    355                 360                 365

CTC GCC AAG CTG GCC GGC GGC GTC TGC GTG ATC CGC GTC GGC GCG GCC     1152
Leu Ala Lys Leu Ala Gly Gly Val Cys Val Ile Arg Val Gly Ala Ala
        370                 375                 380

ACC GAG GTC GAG CTG AAG GAG CGC AAG CAC CGT CTG GAG GAC GCC ATC     1200
Thr Glu Val Glu Leu Lys Glu Arg Lys His Arg Leu Glu Asp Ala Ile
385                 390                 395                 400

TCC GCG ACC CGC GCC GCG GTC GAG GAG GGC ATC GTC TCC GGT GGT GGC     1248
Ser Ala Thr Arg Ala Ala Val Glu Glu Gly Ile Val Ser Gly Gly Gly
```

```
                     405                410                415
TCC GCG CTG GTC CAC GCC GTC AAG GTC CTG GAC GAC AAC CTC GGC CGC    1296
Ser Ala Leu Val His Ala Val Lys Val Leu Asp Asp Asn Leu Gly Arg
            420                425                430

ACC GGC GAC GAG GCC ACC GGT GTC                                    1320
Thr Gly Asp Glu Ala Thr Gly Val
        435                440

(2) INFORMATION FOR SEQ ID NO:9:

(i) SEQUENCE CHARACTERISTICS:
        (A) LENGTH: 2167 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCGGCCGGGC TGAGGTTGGC TGGCTGGCCG GGTTCGGCCG GTGGGTCGAG GTGGCCTGGC      60

CGGGCTCGCC AGGGTGAGTT GGCCGAGCCG AGGCGGCCCC GGGGCTCCCC GGGCCGAGTT     120

GCGCGGCCAG GCCAGGGCTC AGCAGGGTGG GGGAGTGGGG CAGGCGGCCC GGTAGGGGAG     180

TGCGGGAGGG CAGCGCGCGC CGCGCGCATT GGCACTCCGC TTGACCGAGT GCTAATCGCG     240

GTCATAGTCT CAGCTCTGGC ACTCCCCGCA GGAGAGTGCC AACACAGCGA CGGGCAGGTC     300

CCGGCACCCG CGACGACGGA TCGACCTGGT CGCCACACTC AGATCAGTTA ACCCCGTGAT     360

CTCCGAAGGG GGAGGTCGGA TCGTGACGAC CGCCAGCTCC AAGGTTGCCA TCAAGCCGCT     420

CGAGGACCGC ATCGTGGTCC AGCCGCTCGA CGCCGAGCAG ACCACGGCTT CGGGCCTGGT     480

CATCCCGGAC ACCGCGAAGG AGAAGCCCCA GGAGGGCGTC GTCCTCGCGG TCGGCCCGGG     540

CCGCTTCGAG AACGGCGAGC GCCTGCCGCT CGACGTCAAG ACCGGCGACG TCGTGCTGTA     600

CAGCAAGTAC GGCGGCACCG AGGTCAAGTA CAACGGCGAG GAGTACCTCG TCCTCTCGGC     660

CCGCGACGTT CTCGCCATCA TCGAGAAGTA GCAGGCCGGA GCGGTCCGGG CGCGAGCCCG     720

GACGGCAGAC TCCACCTTTT TCCTGAAGCG CGCCCCTGGC CCCCGCGAGT GTTTGCCGGG     780

TGGCGAGGGG CGCGTTTCAT TTCGAGAGCG CGGCGGCAGG CCGCTCCGAG AGGATTCGAA     840

AAGCTCCCAT GGCGAAGATT CTGAAGTTCG ACGAGGACGC CCGTCGCGCC CTTGAGCGCG     900

GCGTGAACCA GCTGGCCGAC ACCGTCAAGG TGACCATCGG CCCCAAGGGC CGCAACGTCG     960

TCATCGACAA GAAGTTCGGC GCCCCGACCA TCACCAACGA CGGCGTCACC ATCGCCCGTG    1020

AGGTCGAGTG CGACGACCCG TACGAGAACC TCGGCGCCCA GCTCGTCAAG GAGGTGGCGA    1080

CCAAGACCAA CGACATCGCG GGTGACGGCA CCACCACCGC GACCGTGCTG GCCCAGGCGC    1140

TGGTCCGCGA GGGCCTGCGC AACGTCGCCG CCGGCGCCTC CCCGGCCGCC CTGAAGAAGG    1200

GCATCGACGC CGCCGTCGCC GCCGTCTCCG CCGAGCTGCT CGACACCGCG CGCCCGATCG    1260

ACGACAAGTC CGACATCGCC GCCGTCGCCG CGCTCTCCGC GCAGGACAAG CAGGTCGGCG    1320

AGCTCATCGC CGAGGCGATG GACAAGGTCG GCAAGGACGG TGTCATCAAC GTCGAGGAGT    1380

CCAACACCTT CGGTGTCGAC CTGGACTTCA CCGAGGGCAT GGCCTTCGAC AAGGGCTACC    1440

TGTCCCCGTA CATGGTGACC GACCAGGAGC GTATGGAGGC CGTCCTCGAC GACCCGTACA    1500

TCCTGATCCA CCAGGGCAAG ATCGGTTCGA TCCAGGACCT GCTGCCGCTG CTGGAGAAGG    1560

TCATCCAGGC GGGTGGCTCC AAGCCGCTGC TGATCATCGC CGAGGACGTC GAGGGCGAGG    1620

CCCTGTCGAC CCTGGTGGTC AACAAGATCC GCGGCACGTT CAACGCCGTC GCCGTCAAGG    1680
```

-continued

```
CGCCCGGCTT CGGTGACCGC CGCAAGGCGA TGCTCGGCGA CATGGCCACC CTCACCGGTG    1740

CCACCGTCAT CGCCGAGGAG GTCGGCCTCA AGCTCGACCA GGCCGGTCTG GACGTGCTGG    1800

GCACCGCCCG CCGCGTCACC GTCACCAAGG ACGACACGAC CATCGTGGAC CTGGAGAAGG    1860

ACGCCGAGGA CGTCCAGGGC CGCGTCGCCC AGATCAAGGC CGAGATCGAG TCGACCGACT    1920

CGGACTGGGA CCGCGAGAAG CTCCAGGAGC GCCTCGCCAA GCTGGCCGGC GGCGTCTGCG    1980

TGATCCGCGT CGGCGCGGCC ACCGAGGTCG AGCTGAAGGA GCGCAAGCAC CGTCTGGAGG    2040

ACGCCATCTC CGCGACCCGC GCCGCGGTCG AGGAGGGCAT CGTCTCCGGT GGTGGCTCCG    2100

CGCTGGTCCA CGCCGTCAAG GTCCTGGACG ACAACCTCGG CCGCACCGGC GACGAGGCCA    2160

CCGGTGT                                                              2167
```

(2) INFORMATION FOR SEQ ID NO:10:

(i) SEQUENCE CHARACTERISTICS:
        (A) LENGTH: 1620 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1620

(xi) SEQUENCE DESCRIPTION: SEQ ID NO:10:

```
ATG GCG AAG ATT CTG AAG TTC GAC GAG GAC GCC CGT CGC GCC CTT GAG     48
Met Ala Lys Ile Leu Lys Phe Asp Glu Asp Ala Arg Arg Ala Leu Glu
 1               5                  10                  15

CGC GGC GTG AAC CAG CTG GCC GAC ACC GTC AAG GTG ACC ATC GGC CCC     96
Arg Gly Val Asn Gln Leu Ala Asp Thr Val Lys Val Thr Ile Gly Pro
             20                  25                  30

AAG GGC CGC AAC GTC GTC ATC GAC AAG AAG TTC GGC GCC CCG ACC ATC    144
Lys Gly Arg Asn Val Val Ile Asp Lys Lys Phe Gly Ala Pro Thr Ile
         35                  40                  45

ACC AAC GAC GGC GTC ACC ATC GCC CGT GAG GTC GAG TGC GAC GAC CCG    192
Thr Asn Asp Gly Val Thr Ile Ala Arg Glu Val Glu Cys Asp Asp Pro
     50                  55                  60

TAC GAG AAC CTC GGC GCC CAG CTC GTC AAG GAG GTG GCG ACC AAG ACC    240
Tyr Glu Asn Leu Gly Ala Gln Leu Val Lys Glu Val Ala Thr Lys Thr
 65                  70                  75                  80

AAC GAC ATC GCG GGT GAC GGC ACC ACC ACC GCG ACC GTG CTG GCC CAG    288
Asn Asp Ile Ala Gly Asp Gly Thr Thr Thr Ala Thr Val Leu Ala Gln
                 85                  90                  95

GCG CTG GTC CGC GAG GGC CTG CGC AAC GTC GCC GCC GGC GCC TCC CCG    336
Ala Leu Val Arg Glu Gly Leu Arg Asn Val Ala Ala Gly Ala Ser Pro
            100                 105                 110

GCC GCC CTG AAG AAG GGC ATC GAC GCC GCC GTC GCC GCC GTC TCC GCC    384
Ala Ala Leu Lys Lys Gly Ile Asp Ala Ala Val Ala Ala Val Ser Ala
        115                 120                 125

GAG CTG CTC GAC ACC GCG CGC CCG ATC GAC GAC AAG TCC GAC ATC GCC    432
Glu Leu Leu Asp Thr Ala Arg Pro Ile Asp Asp Lys Ser Asp Ile Ala
    130                 135                 140

GCC GTC GCC GCG CTC TCC GCG CAG GAC AAG CAG GTC GGC GAG CTC ATC    480
Ala Val Ala Ala Leu Ser Ala Gln Asp Lys Gln Val Gly Glu Leu Ile
145                 150                 155                 160

GCC GAG GCG ATG GAC AAG GTC GGC AAG GAC GGT GTC ATC ACC GTC GAG    528
Ala Glu Ala Met Asp Lys Val Gly Lys Asp Gly Val Ile Thr Val Glu
                165                 170                 175
```

```
GAG TCC AAC ACC TTC GGT GTC GAC CTG GAC TTC ACC GAG GGC ATG GCC         576
Glu Ser Asn Thr Phe Gly Val Asp Leu Asp Phe Thr Glu Gly Met Ala
        180                 185                 190

TTC GAC AAG GGC TAC CTG TCC CCG TAC ATG GTG ACC GAC CAG GAG CGT         624
Phe Asp Lys Gly Tyr Leu Ser Pro Tyr Met Val Thr Asp Gln Glu Arg
            195                 200                 205

ATG GAG GCC GTC CTC GAC GAC CCG TAC ATC CTG ATC CAC CAG GGC AAG         672
Met Glu Ala Val Leu Asp Asp Pro Tyr Ile Leu Ile His Gln Gly Lys
    210                 215                 220

ATC GGT TCG ATC CAG GAC CTG CTG CCG CTG CTG GAG AAG GTC ATC CAG         720
Ile Gly Ser Ile Gln Asp Leu Leu Pro Leu Leu Glu Lys Val Ile Gln
225                 230                 235                 240

GCG GGT GGC TCC AAG CCG CTG CTG ATC ATC GCC GAG GAC GTC GAG GGC         768
Ala Gly Gly Ser Lys Pro Leu Leu Ile Ile Ala Glu Asp Val Glu Gly
                245                 250                 255

GAG GCC CTG TCG ACC CTG GTG GTC AAC AAG ATC CGC GGC ACG TTC AAC         816
Glu Ala Leu Ser Thr Leu Val Val Asn Lys Ile Arg Gly Thr Phe Asn
            260                 265                 270

GCC GTC GCC GTC AAG GCG CCC GGC TTC GGT GAC CGC CGC AAG GCG ATG         864
Ala Val Ala Val Lys Ala Pro Gly Phe Gly Asp Arg Arg Lys Ala Met
    275                 280                 285

CTC GGC GAC ATG GCC ACC CTC ACC GGT GCC ACC GTC ATC GCC GAG GAG         912
Leu Gly Asp Met Ala Thr Leu Thr Gly Ala Thr Val Ile Ala Glu Glu
290                 295                 300

GTC GGC CTC AAG CTC GAC CAG GCC GGT CTG GAC GTG CTG GGC ACC GCC         960
Val Gly Leu Lys Leu Asp Gln Ala Gly Leu Asp Val Leu Gly Thr Ala
305                 310                 315                 320

CGC CGC GTC ACC GTC ACC AAG GAC GAC ACG ACC ATC GTG GAC GGC GGC        1008
Arg Arg Val Thr Val Thr Lys Asp Asp Thr Thr Ile Val Asp Gly Gly
                325                 330                 335

GGC AAC GCC GAG GAC GTC CAG GGC CGC GTC GCC CAG ATC AAG GCC GAG        1056
Gly Asn Ala Glu Asp Val Gln Gly Arg Val Ala Gln Ile Lys Ala Glu
            340                 345                 350

ATC GAG TCG ACC GAC TCG GAC TGG GAC CGC GAG AAG CTC CAG GAG CGC        1104
Ile Glu Ser Thr Asp Ser Asp Trp Asp Arg Glu Lys Leu Gln Glu Arg
    355                 360                 365

CTC GCC AAG CTG GCC GGC GGC GTC TGC GTG ATC CGC GTC GGC GCG GCC        1152
Leu Ala Lys Leu Ala Gly Gly Val Cys Val Ile Arg Val Gly Ala Ala
370                 375                 380

ACC GAG GTC GAG CTG AAG GAG CGC AAG CAC CGT CTG GAG GAC GCC ATC        1200
Thr Glu Val Glu Leu Lys Glu Arg Lys His Arg Leu Glu Asp Ala Ile
385                 390                 395                 400

TCC GCG ACC CGC GCC GCG GTC GAG GAG GGC ATC GTC TCC GGT GGT GGC        1248
Ser Ala Thr Arg Ala Ala Val Glu Glu Gly Ile Val Ser Gly Gly Gly
                405                 410                 415

TCC GCG CTG GTC CAC GCC GTC AAG GTC CTG GAC GAC AAC CTC GGC CGC        1296
Ser Ala Leu Val His Ala Val Lys Val Leu Asp Asp Asn Leu Gly Arg
            420                 425                 430

ACC GGC GAC GAG GCC ACC GGT GTC GCG GTC GTC CGC CGC GCC GCC GTC        1344
Thr Gly Asp Glu Ala Thr Gly Val Ala Val Val Arg Arg Ala Ala Val
    435                 440                 445

GAG CCG CTG CGC TGG ATC GCC GAG AAC GCC GGC CTC GAG GGC TAC GTC        1392
Glu Pro Leu Arg Trp Ile Ala Glu Asn Ala Gly Leu Glu Gly Tyr Val
450                 455                 460

ATC ACC ACC AAG GTG GCG GAG CTC GAC AAG GGC CAG GGC TTC AAC GCG        1440
Ile Thr Thr Lys Val Ala Glu Leu Asp Lys Gly Gln Gly Phe Asn Ala
465                 470                 475                 480

GCC ACC GGC GAG TAC GGC GAC CTG GTC AAG GCC GGC GTC ATC GAC CCG        1488
Ala Thr Gly Glu Tyr Gly Asp Leu Val Lys Ala Gly Val Ile Asp Pro
                485                 490                 495
```

| | | | | | | | | | | | | | | | | |
|---|---|---|---|---|---|---|---|---|---|---|---|---|---|---|---|---|
| GTC | AAG | GTC | ACC | GCG | TCC | GCC | CTG | GAG | AAC | GCG | GCC | TCC | ATC | GCC | TCC | 1536 |
| Val | Lys | Val | Thr | Ala | Ser | Ala | Leu | Glu | Asn | Ala | Ala | Ser | Ile | Ala | Ser | |
| | | 500 | | | | | 505 | | | | | 510 | | | | |
| CTG | CTC | CTG | ACG | ACC | GAG | ACC | CTG | GTC | GTC | GAG | AAG | CCG | GCC | GAG | GAG | 1584 |
| Leu | Leu | Leu | Thr | Thr | Glu | Thr | Leu | Val | Val | Glu | Lys | Pro | Ala | Glu | Glu | |
| | | | 515 | | | | | 520 | | | | | 525 | | | |
| GAG | CCC | GAG | GCC | GGT | CAC | GGT | CAC | GGG | CAC | AGC | CAC | | | | | 1620 |
| Glu | Pro | Glu | Ala | Gly | His | Gly | His | Gly | His | Ser | His | | | | | |
| | | 530 | | | | | 535 | | | | | 540 | | | | |

(2) INFORMATION FOR SEQ ID NO:11:

(i) SEQUENCE CHARACTERISTICS:
        (A) LENGTH: 2668 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CCGGCCGGGC TGAGGTTGGC TGGCTGGCCG GGTTCGGCCG GTGGGTCGAG GTGGCCTGGC      60

CGGGCTCGCC AGGGTGAGTT GGCCGAGCCG AGGCGGCCCC GGGGCTCCCC GGGCCGAGTT     120

GGCGCGGCCA GGCCAGGGCT CAGCAGGGTG GGGGAGTGGG GCAGGCGGCC CGGTAGGGGA     180

GTGCGGGAGG GCAGCGCGCG CCGCGCGCAT TGGCACTCCG CTTGACCGAG TGCTAATCGC     240

GGTCATAGTC TCAGCTCTGG CACTCCCCGC AGGAGACTGC CAACACAGCG ACGGGCAGGT     300

CCGGCACCCG CGACGACGGA TCGACCTGGT CGCCACACTC AGATCAGTTA ACCCCGTGAT     360

CTCCGAAGGG GGAGGTCGGA TCGTGACGAC CGCCAGCTCC AAGGTTGCCA TCAAGCCGCT     420

CGAGGACCGC ATCGTGGTCC AGCCGCTCGA CGCCGAGCAG ACCACGGCTT CGGGCCTGGT     480

CATCCCGGAC ACCGCGAAGG AGAAGCCCCA GGAGGGCGTC GTCCTCGCGG TCGGCCCGGG     540

CCGCTTCGAG AACGGCGAGC GCCTGCCGCT CGACGTCAAG ACCGGCGACG TCGTGCTGTA     600

CAGCAAGTAC GGCGGCACCG AGGTCAAGTA CAACGGCGAG GAGTACCTCG TCCTCTCGGC     660

CCGCGACGTT CTCGCCATCA TCGAGAAGTA GCAGGCCGGA GCGGTCCGGG CGCGAGCCCG     720

GACGGCAGAC TCCACCTTTT TCCTGAAGCG CGCCCCTGGC CCCCGCGAGT GTTTGCCGGG     780

TGGCGAGGGG CGCGTTTCAT TTCGAGAGCG CGGCGGCAGG CCGCTCCGAG AGGATTCGAA     840

AAGCTCCCAT GGCGAAGATT CTGAAGTTCG ACGAGGACGC CCGTCGCGCC CTTGAGCGCG     900

GCGTGAACCA GCTGGCCGAC ACCGTCAAGG TGACCATCGG CCCCAAGGGC CGCAACGTCG     960

TCATCGACAA GAAGTTCGGC GCCCCGACCA TCACCAACGA CGGCGTCACC ATCGCCCGTG    1020

AGGTCGAGTG CGACGACCCG TACGAGAACC TCGGCGCCCA GCTCGTCAAG GAGGTGGCGA    1080

CCAAGACCAA CGACATCGCG GGTGACGGCA CCACCACCGC GACCGTGCTG GCCCAGGCGC    1140

TGGTCCGCGA GGGCCTGCGC AACGTCGCCG CCGGCGCCTC CCCGGCCGCC CTGAAGAAGG    1200

GCATCGACGC CGCCGTCGCC GCCGTCTCCG CCGAGCTGCT CGACACCGCG CGCCCGATCG    1260

ACGACAAGTC CGACATCGCC GCCGTCGCCG CGCTCTCCGC GCAGGACAAG CAGGTCGGCG    1320

AGCTCATCGC CGAGGCGATG GACAAGGTCG GCAAGGACGG TGTCATCAAC GTCGAGGAGT    1380

CCAACACCTT CGGTGTCGAC CTGGACTTCA CCGAGGGCAT GGCCTTCGAC AAGGGCTACC    1440

TGTCCCCGTA CATGGTGACC GACCAGGAGC GTATGGAGGC CGTCCTCGAC GACCCGTACA    1500

TCCTGATCCA CCAGGGCAAG ATCGGTTCGA TCCAGGACCT GCTGCCGCTG CTGGAGAAGG    1560

TCATCCAGGC GGGTGGCTCC AAGCCGCTGC TGATCATCGC CGAGGACGTC GAGGGCGAGG    1620
```

```
CCCTGTCGAC CCTGGTGGTC AACAAGATCC GCGGCACGTT CAACGCCGTC GCCGTCAAGG    1680

CGCCCGGCTT CGGTGACCGC CGCAAGGCGA TGCTCGGCGA CATGGCCACC CTCACCGGTG    1740

CCACCGTCAT CGCCGAGGAG GTCGGCCTCA AGCTCGACCA GGCCGGTCTG GACGTGCTGG    1800

GCACCGCCCG CCGCGTCACC GTCACCAAGG ACGACACGAC CATCGTGGAC CTGGAGAAGG    1860

ACGCCGAGGA CGTCCAGGGC CGCGTCGCCC AGATCAAGGC CGAGATCGAG TCGACCGACT    1920

CGGACTGGGA CCGCGAGAAG CTCCAGGAGC GCCTCGCCAA GCTGGCCGGC GGCGTCTGCG    1980

TGATCCGCGT CGGCGCGGCC ACCGAGGTCG AGCTGAAGGA GCGCAAGCAC CGTCTGGAGG    2040

ACGCCATCTC CGCGACCCGC GCCGCGGTCG AGGAGGGCAT CGTCTCCGGT GGTGGCTCCG    2100

CGCTGGTCCA CGCCGTCAAG GTCCTGGACG ACAACCTCGG CCGCACCGGC GACGAGGCCA    2160

CCGGTGTCGC GGTCGTCCGC CGCGCCGCCG TCGAGCCGCT GCGCTGGATC GCCGAGAACG    2220

CCGGCCTCGA GGGCTACGTC ATCACCACCA AGGTGGCGGA GCTCGACAAG GGCCAGGGCT    2280

TCAACGCGGC CACCGGCGAG TACGGCGACC TGGTCAAGGC CGGCGTCATC GACCCGGTCA    2340

AGGTCACCCG CTCCGCCCTG GAGAACGCGG CCTCCATCGC CTCCCTGCTC CTGACGACCG    2400

AGACCCTGGT CGTCGAGAAG CCGGCCGAGG AGGAGCCCGA GGCCGGTCAC GGTCACGGGC    2460

ACAGCCACTG AGGCTGACCC CTTCCGCAGC CGAGGCCCGG CTCCCCGTCG CGGGGAGCCG    2520

GGCCTCCGGC GTGTCCGGGA CCCCCCGGGA CGCGCGACGC CTACCGCGGC CCGTACTTGC    2580

GGCCGGTACG CGAGGTCATC CCGGTCAGCA GGGCCCGCGG GGTCAGCTTC ACCAGGCCCA    2640

TCAGCGCCTT GTACCGAGGG TCCGGGAT                                      2668

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Asp Asp Pro Tyr Glu Asn Leu Gly Ala Gln
1               5                   10

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9
        (D) OTHER INFORMATION: /note= "Nucleotide 9 wherein S is C
            or G."

(ix) FEATURE:
        (A) NAME/KEY: misc_feature
        (B) LOCATION: 21
        (D) OTHER INFORMATION: /note= "Nucleotide 21 wherein S is
            C or G."

(ix) FEATURE:
        (A) NAME/KEY: misc_feature
        (B) LOCATION: 27
```

-continued (D) OTHER INFORMATION: /note= "Nucleotide 27 wherein Y is
            C or T."

(xi) SEQUENCE DESCRIPTION: SEQ ID NO:13:

GACGACCCST ACGAGAACCT SGGCGCYCA                                              29

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9
        (D) OTHER INFORMATION: /note= "Nucleotide 9 wherein S is C
            or G."

(ix) FEATURE:
        (A) NAME/KEY: misc_feature
        (B) LOCATION: 21
        (D) OTHER INFORMATION: /note= "Nucleotide 21 wherein S is
            C or G."

(ix) FEATURE:
        (A) NAME/KEY: misc_feature
        (B) LOCATION: 27
        (D) OTHER INFORMATION: /note= "Nucleotide 27 wherein R is
            G or A."

(xi) SEQUENCE DESCRIPTION: SEQ ID NO:14:

CTGCTGGGSA TGCTCTTGGA SCCGCGRGTC                                             30

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gly His Gly His Gly His Ser His
1               5

What is claimed is:

1. A recombinant nucleotide sequence comprising:

(a) a regulatory sequence of initiation of transcription wherein said regulatory sequence includes a promoter having a sequence in association with a motif GCACTC 9N GAGTGC (SEQ ID NO: 1) in which N is any one of the four bases, thymine, guanine, adenine and cytosine; and (b) a sequence coding for a heterologous polypeptide wherein said coding sequence is positioned downstream from said regulatory sequence at a site which allows said heterologous polypeptide to be expressed under the control of said promoter.

2. The nucleotide sequence according to claim 1, wherein said promoter is a promoter associated with a heat shock protein.

3. The nucleotide sequence according to claim 1, wherein the GCACTC 9N GAGTGC (SEQ ID NO: 1) sequence is included, at least in part, within the sequence of the promoter.

4. The nucleotide sequence according to claim 2, wherein the promoter is selected from the following sequences:

P1 corresponding to one of the sequences (SEQ ID NO: 2–3):

5' CATTGGCACTCCGCTTGACCGAGTGCTAATCGCGGTCATAGTCTCAGCTC

3' TG or

-continued

```
GCATTGGCACTCCGCTTGACCGAGTGCTAATCGCGGTCATAGTCTCAGCT
5'

CTG
3'
```

P2 corresponding to one of the sequences (SEQ ID NO: 4–5):

```
GGAGGCCCCTAGCGCCTGCACTCTC-
CTACCCCGAGTGCTATTATTGGCGT 5'TA 3' or GGAG-
GCCCCTAGCGCCTGCACTCTCCTAC-
     CCCGAGTGCTAATTATTGGCG 5'TTA.   3'
```

5. The nucleotide sequence according to claim 1, wherein the motif GCACTC 9N GAGTGC (SEQ ID NO: 1) is distinct from the sequence of the promoter.

6. The nucleotide sequence according to claim 1, wherein the GCATC 9N GAGTGC motif (SEQ ID NO: 1) is located upstream from the sequence of the promoter.

7. An expression vector comprising a recombinant nucleotide sequence according to claim 1, which expresses said heterologous polypeptide.

8. The expression vector according to claim 7, which is a plasmid.

9. A cell transformed by the expression vector according to claims 7 or 8.

10. The cell according to claim 9, which is a prokaryotic cell.

11. A process for producing a polypeptide comprising the steps of:
   a) transforming a cell with the expression vector of claims 7 or 8 under conditions such that said heterologous polypeptide is expressed; and
   b) recovering said heterologous polypeptide that is expressed.

12. The process according to claim 11, wherein the conditions allowing expression of said polypeptide include application of a heat shock.

13. The process according to claim 11, wherein the cell is a prokaryotic cell.

14. A process for conferring a thermoinducible character on a promoter comprising the steps of:
   positioning a sequence comprising a motif GCACTC 9N GAGTGC (SEQ ID NO: 1) upstream from a promoter; or
   inserting a sequence containing a GCACTC 9N GAGTGC motif (SEQ ID NO: 1) at a site within the promoter wherein said site is selected such that the site does not perturb the activity of the promoter.

15. The process according to claim 14, wherein the promoter is a promoter present in Actinomycetes.

16. A regulatory sequence comprising a promoter in association with a motif GCACTC 9N GAGTGC (SEQ ID NO: 1) wherein N is thymine or guanine, adenine or cytosine wherein said regulatory sequence lacks the coding sequence normally associated with said promoter.

17. A regulatory sequence comprising one of the following sequences:

```
CATTGGCACTCCGCTTGACCGAGTGCTAATCGCGGTCATAGTCTCAGCTC
5'

TG
3' or

GCATTGGCACTCCGCTTGACCGAGTGCTAATCGCGGTCATAGTCTCAGCT
5'

CTG
3'
```

18. A recombinant nucleotide sequence comprising:
   (a) a regulatory sequence of initiation of transcription wherein said regulatory sequence includes a promoter selected from the following sequences:

```
CATTGGCACTCCGCTTGACCGAGTGCTAATCGCGGTCATAGTCTCAGCTC
5'

TG
3' or

GCATTGGCACTCCGCTTGACCGAGTGCTAATCGCGGTCATAGTCTCAGCT
5'

CTG
3'
``` in association with a motif GCACTC 9N GAGTGC (SEQ ID NO: 1) in which N is any one of the four bases, thymine, guanine adenine and cytosine; and (b) a sequence coding for a heterologous polypeptide wherein said coding sequence is positioned downstream from said regulatory sequence at a site which allows said heterologous polypeptide to be expressed under the control of said promoter.

19. A recombinant nucleotide sequence comprising:
   (a) a regulatory sequence of initiation of transcription wherein said regulatory sequence includes a promoter having a sequence in association with a motif GCACTC 9N GAGTGC (SEQ ID NO: 1) in which N is any one of the four bases, thymine, guanine, adenine and cytosine and wherein said motif confers thermoinducibility on said promoter; and (b) a sequence coding for heterologous polypeptide wherein said coding sequence is positioned downstream from said regulatory sequence at a site which allows said heterologous polypeptide to be expressed under the control of said promoter.

\* \* \* \* \*